United States Patent [19]
Bao et al.

[11] Patent Number: 6,020,121
[45] Date of Patent: Feb. 1, 2000

[54] INHIBITORS OF REGULATORY PATHWAYS

[75] Inventors: Ying Bao, Sunnyvale; Amy Boggs, Menlo Park; Pamela R. Contag, San Jose; Nancy A. Federspiel; Alan Hebert, both of Menlo Park; Scott Hecker; Francois Malouin, both of Los Gatos, all of Calif.

[73] Assignee: Microcide Pharmaceuticals, Inc., Mountain View, Calif.

[21] Appl. No.: 08/672,215

[22] Filed: Jun. 25, 1996

Related U.S. Application Data

[60] Provisional application No. 60/004,626, Sep. 29, 1995.

[51] Int. Cl.[7] .............................. C12Q 1/00; C12Q 1/68; C12N 1/38; C12N 15/31
[52] U.S. Cl. .............................. 435/4; 435/6; 435/252.1; 536/23.7; 536/24.1
[58] Field of Search ........................... 514/340, 2; 435/6, 435/4, 252.1; 536/23.7, 24.1

[56] References Cited

FOREIGN PATENT DOCUMENTS 9426262  11/1994  WIPO .

OTHER PUBLICATIONS

Regassa et al. Glucose and nonmaintained pH decrease expression of the accessory gene regulator (agr) in *Staphylococcus arueus*. Infection and Immunity vol. 60 pp. 3381–3388, 1992.

Wang and Novick, "Nucleoside Sequence and Expression of the β–Lactamase Gene from *Staphylococcus aureus* Plasmid P1258 in *Escherichia coli, Bacillus subtilis,* and *Staphylococcus aureus," J. Bacteriology* 169:1763–1766 (1987).

Wanner, "Ch. 82—Phosphate Regulation of Gene Expression in *Escherichia coli, " Escherichia Coli* and *Salmonella Typhimurium: Cellular and Molecular Biology,* Neidhardt et al. editors, American Society for Microbiology, Washington, D.C. pp. 1326–1333 (1987).

Wright et al., "Purification and Characterization of VanR and the Cytosolic Domain of VanS: A Two–Component Regulatory System Required for Vancomycin Resistance in *Enterococcus faecium* BM4147," *Biochemistry* 32:5057–5063 (1993).

Yoshikawa et al., "Pleiotropic Alteration of Activities of Several Toxins and Enzymes in Mutants of *Staphylococcus aureus," J. Bacteriol.* 119:117–122 (1974).

Peng et al., "Cloning, Characterization, and Sequencing of an Accessory gene Regulator (agr) in *Staphylococcus aureus," J. Bacteriology* 170:4365–4372 (1988).

Piggot and Curtis, "Analysis of the Regulation of Gene Expression during *Bacillus subtilis* Sporulation by Manipulation of the Copy Number of spo–lacZ Fusions," *J. Bacteriology* 169:1260–1266 ((1987).

Projan et al., "Glycerol Monolaurate Inhibits the Production of β–Lactamase, Toxic Shock Syndrome Toxin–1, and Other Staphylococcal Exoproteins by Interfering with Signal Transduction," *J. Bacteriology* 176:4204–4209 (1994).

Recsei et al., "Regulation of exoprotein gene expression in *Staphylococcus aureus* by agr," *Mol. Gen. Genet.* 202:58–61 (1986).

Rich et al., "Genetic Evidence that the gacA Gene Encodes the Cognate Response Regulator for the lemA Sensor in *Pseudomonas syringae," J. Bacteriology* 176:7468–7475 (1994).

Rosey et al., "Lactose Metabolism by *Staphylococcus aureus:* Characterization of lacABCD, the Structural Genes of the Tagatose 6–Phosphate Pathway," *J. Bacteriology* 173:5992–5998 (1991).

Roychoudhury et al., "Inhibitors of two–component signal transduction systems: Inhibition of alginate gene activation in *Pseudomonas aeruginosa," Proc. Natl. Acad. Sci. USA* 90:965–969.

Schlievert et al., "Effect of Glycerol Monolaurate on Bacterial Growth and Toxin Production," *Antimicrob. Agents Chemother.* 36:626–631 (1992).

Seki et al., "Cloning and Nucleotide Sequence of phoP, the Regulatory Gene for Alkaline Phosphatase and Phosphodiesterase in *Bacillus subtilis," J. Bacteriology* 169:2913–2916 (1987).

Shortle, "A genetic system for analysis of Staphylococcal nuclease," *Gene* 22:181–189 (1983).

Silver and Walderhaug, "Gene Regulation of Plasmid– and Chromosome–Determined Inorganic Ion Transport in Bacteria," *Microbiological Reviews* 56:195–228 (1992).

Simoni et al., "Sugar Transport: IV: Isolation and Characterization of the Lactose Phosphotransferase System in *Staphylococcus Aureus," J. Biol. Chem.* 248:932–940 (1973).

Smeltzer et al., "Quantitative Spectrophotometric Assay for Staphylococcal Lipase," *Applied and Env. Microbiol.* 58:2815–2819 (1992).

Smeltzer et al., "Phenotypic Characterization of xpr, a Global Regulator of Extracellular Virulence Factors in *Staphylococcus aureus," Infection and Immunity* 61:919–925 (1993).

Smith, "Ch. 9—The Initiation of Sporulation," in *Regulation of Procaryotic Development,* Smith et al. editors, American Society for Microbiology, Washington, D.C. pp. 185–210 (1989).

Soro et al., "Phosphatase Activity of Staphylococci is Constitutive in Some Species and Repressed by Phosphates in Others," *J. Clin. Microbiol.* 228:2707–2710 (1990).

Stewart and Dahlquist, "Molecular Components of Bacterial Chemotaxis," *Chem. Rev.* 87:997–1025 (1987).

(List continued on next page.)

*Primary Examiner*—John S. Brusca
*Attorney, Agent, or Firm*—Lyon & Lyon LLP

[57] ABSTRACT

Methods are provided for screening for potential inhibitors of bacterial, or other microbial, global pathogenesis gene regulators and other gene regulators. Methods are also provided for treating microbial (e.g., bacterial) infections using such inhibitors. Also included are pharmaceutical compositions containing such inhibitors. The screening methods involve detecting whether the activity of a global pathogenesis gene regulator is altered in the presence of a test compound.

15 Claims, 19 Drawing Sheets

OTHER PUBLICATIONS

Stock et al., "Protein Phosphorylation and Regulation of Adaptive Responses in Bacteria," *Microbiol. Rev.* 53:450–490 (1989).

Tesch et al., "Evidence of a Novel Staphylococcal mec–Encoded Element (mecR) Controlling Expression of Penicillin–Binding Protein 2'," *Antimicrob. Agents Chemother.* 34:1703–1706 (1990).

Vandenesch et al., "Agr–related sequences in *Staphylococcus lugdunensis*," *FEMS Microbiology Letters* 111:115–122 (1993).

Wang et al., "Nucleotide seqence of β–lactamase regulatory genes from staphylococcal plasmid pI258," *Nucleic Acids Research* 19:4000 (1991).

Lorian, "Medical relevance of low concentrations of antibiotics," *J. Antimicrob. Chemother.* 31 (Supl. D):137–148 (1993).

Losick et al., "Genetics of Endospore Formation in *Bacillus Subtilis*," *Annu. Rev. Genet.* 20:625–669 (1986).

MacNab, "Ch. 49—Motility and Chemotaxis," in *Excherichia Coli and Salmonella Typhimurium: Cellular and Molecular Biology*, F.C. Neidhardt et al. editors, American Society for Microbiology, Washington, D.C., pp. 732–659 (1987).

Malouin et al., "Outer Membrane and Porin Characteristics of *Serratia marcescens* Grown In Vitro and in Rat Intraperitoneal Diffusion Chambers," *Infect. Immun.* 58:1247–1253 (1990).

Miller et al., "Coordinate Regulation and Sensory Transduction in the Control of Bacterial Virulence," *Science* 243:916–921 (1989).

Morgan et al., "Proteins Antigentically Related to Methyl-Accepting Chemotaxis Proteins of *Escherchia coli* Detected in a Wide Range of Bacterial Species," *J. Bacteriology* 175:133–140 (1993).

Mühldörfer and Hacker, "Genetics aspects of *Escherichia coli* virulence," *Microbial Pathogenesis* 16:171–181 (1994).

Nakata et al., "Genetic and Biochemical Analysis of the Phosphate–Specific Transport System in *Escherichia coli*," in *Phosphate Metabolism and Cellular Regulation in Microorganisms*, A. Torriani–Gorini et al. editors, American Society for Microbiology, Washington, D.C., pp. 150–155 (1987).

Nesin et al., "Cloning and Nucleotide Sequence of a Chromosomally Encoded Tetracycline Resistance Determinant, tetA(M), from a Pathogenic, Methicillin–Resistant Strain of *Staphylococcus aureus*," *Antimicrobial Agents Chemotherapy* 34:2273–2276 (1990).

Nicholson and Setlow, "Ch. 9—Sporulation, Germination and Outgrowth," in *Molecular Biology Methods for Bacillus*, Harwood and Cutting editors, John Wiley and Sons, Ltd., Chichester, West Sussex, England, pp. 391–429 (1990).

Novick et al., "The agr P2 operon: an autocatalytic sensory transduction system in *Staphylococcus aureus*," *Mol. Gen Genet* 248:446–458 (1995).

Novick et al., "Synthesis of staphylococcal virulence factors is controlled by a regulatory RNA molecule," *EMBO J.* 12:3967–3975 (1993).

O'Callaghan et al., "Novel Method for Detection of β–Lactamases by Using a Chromogenic Cephalosporin Substrate," *Antimicrob. Agents Chemother.* 1:283–288 (1972).

O'Toole and Foster, "Molecular cloning and expression of the epidermolytic toxin A gene of *Staphylococcus aureus*," *Microbial Pathogenesis* 1:583–594 (1986).

O'Toole and Foster, "Nucleotide Sequence of the Epidermolytic Toxin A Gene of *Staphylococcus aureus*," *J. Bacteriology* 169:3910–3915 (1987).

Parkinson, "cheA, cheB, and cheC Genes of *Escherichia coli* and Their Role in Chemotaxis," *J. Bacteriology* 126:758–770 (1976).

Parkinson and Kofoid, "Communication Modules in Bacterial Signaling Proteins," *Ann. Rev. Genet.* 26:71–112 (1992).

Patel et al., "Virulence of Protein A–Deficient and Alpha–Toxin–Deficient Mutants of *Staphylococcus aureus* Isolated by Allele Replacement," *Infection and Immunity* 55:3103–3110 (1987).

Patti et al., "The *Staphylococcus aureus* Collagen Adhesin Is a Virulence Determinant in Experimental Septic Arthritis," *Infection and Immunity* 62:152–561 (1994).

Dargis et al., "Modification in Penicillin–Binding Proteins during In Vivo Development of Genetic Competence of *Haemophilus influenzae* is Associated with a Rapid Change in the Physiological State of Cells," *Infection and Immunity* 60:4024–4031 (1992).

DeLencastre et al., "Molecular aspects of methicillin resistance in *Staphylococcus aureus*," *J. Antimicrob. Chemother.* 33:7–24 (1994).

Eliopolous and Moellering, "Ch. 13—Antimicrobial Combinations," in *Antibiotics in Laboratory Medicine*, 3rd ed., Lorian ed., at pp. 432–492 (1991).

Fitton et al., "The Amino Acid Sequence of the Delta Haemolysin of *Staphylococcus aureus*," *FEBS Letters* 115:209–212 (1980).

Garle et al., "In Vitro Cytotoxicity Tests for the Prediction of Acute Toxicity In Vivo," *Toxic. in Vitro* 8:1303–1312 (1994).

Gaskill et al., "Regulation of the Enteroxtoxin B Gene in *Staphylococcus aureus*," *J. Biol. Chem.* 263:6276–6280 (1988).

Giraudo et al., "Characterization of a TN551–mutant of *Staphylococcus aureus* defective in the production of several exoproteins," *Can. J. Microbiol.* 40:677–681 (1994).

Groisman and Ochman, "How to become a pathogen," *Trends in Microbiology* 2:289–294 (1994).

Hart et al., "The Extracellular Protein Regulator (xpr) Affects Expoprotein and agr mRNA Levels in *Staphylococcus aureus*," *J. Bacteriology* 175:7875–7879 (1993).

Heinrichs et al., "Characterization of the sar Locus and Its Interaction with agr in *Staphylococcus aureus*," *J. Bacteriology* 178:418–423 (1996).

Hiramatsu et al., "Molecular cloning and nucleotide sequence determination of the regulator region of mecA gene in methicillin–resistant *Staphylococcus aureus*," *FEBS Letters* 298:133–136 (1992).

Horinouchi and Weisblum, "Nucleotide Sequence and Functional Map of pE194, a Plasmid That Specifies Inducible Resistance to Macrolide, Lincosamide, and Streptogramin Type B Antibiotics," *J. Bacteriology* 150:804–814 (1982).

Hulett et al., "Sequential Action of Two–Component Genetic Switches Regulates the PHO Regulon in *Bacillus subtilis*," *J. Bacteriol.* 176:1348–1358 (1994).

Janzon et al., "Identification and nucleotide sequence of the delta–lysin gene, hld, adjacent to the accessory gene regulator (agr) of *Staphylococcus aureus*," *Mol Gen Genet* 219:480–485 (1989).

Janzon and Arvidson, "The role of the δ–lysin gene (hld) in the regulation of virulence genes by the accessory gene regulator (agrt) in *Staphylococcus aureus*," *EMBO J.* 9:1391–1399 (1990).

Ji et al., "Cell density control of staphylococcal virulence mediated by an octapeptide pheromone," *Proc. Natl. Acad. Sci. USA* 92:12055–12059 (1995).

Kernodle et al., "Purification of *Staphylococcus aureus* β–Lactamases by Using Sequential Cation–Exchange and Affinity Chromatography," *Antimicrob. Agents Chemother.* 34:2177–2183 (1990).

Kornblum et al., Agr: a polycistronic locus regulating exoprotein synthesis in *Staphylococcus aureus*, pp. 373–402, In R.P. Novick (ed.), *Molecular Biology of the Staphylococci*, VCH Publishers, Inc., New York (1990).

Leighton and Doi, "The Stability of Messenger Ribonucleic Acid during Sporulation in *Bacillus subtilis*," *J. Biol. Chem.* 246:3189–3195 (1971).

Liao et al., "Molecular Characterization of Two Gene Loci Required for Production of the Key Pathogenicity Factor Pectate Lyase in *Pseudomonas viridiflava*," *Mol. Plant Microb. Interact.* 7:391–400 (1994).

Abbas–Ali and Coleman, "The Characteristics of Extracellular Protein Secretion by *Staphylococcus aureus* (Wood 46) and their Relationship to the Regulation of α–Toxin Formation," *J. Gen. Microbiol.* 99:277–282 (1977).

Abdelnour et al., "The Accessory Gene Regulator (agr) Controls *Staphylococcus aureus* Virulence in a Murine Arthritis Model," *Infect. Immun.* 61:3879–3885 (1993).

Adler, "A Method for Measuring Chemotaxis and Use of the Method to Determine Optimum Conditions for Chemotaxis by *Escherichia coli*," *J. Gen. Microbiol.* 74:77–91 (1973).

Arthur et al., "The VansS–VanR Two–Component Regulatory System Controls Synthesis of Depsipeptide Peptidoglycan Precursors in *Enterococcus faecium* BM4147," *J. Bacteriology* 174:2528–2591 (1992).

Axelsson et al., "Cloning and Nucleotide Sequence of a Gene from *Lactobacillus sake* Lb706 Necessary for Sakacin A Production in Immunity," *Appl. Environ. Microbiol.* 59:2868–2875 (1993).

Baddour, "Virulence Factors among Gram–Positive Bacteria in Experimental Endocarditis," *Infection and Immunity* 62:2143–2148 (1994).

Balaban and Novick, "Autocrine regulation of toxin synthesis by *Staphylococcus aureus*," *Proc. Natl. Acad. Sci. USA* 92:1619–1623 (1995).

Bennett and Chopra, "Molecular Basis of β–Lactamase Induction in Bacteria," *Antimicrob. Agents and Chemother.* 37:153–158 (1993).

Bjorklind and Arvidson, "Mutants of *Staphylococcus Aureus* Affected in the Regulation of Exoprotein Synthesis," *FEMS Microbiology Letters* 7:203–206 (1980).

Chambers, "Methicillin–Resistant Staphylococci," *Clin. Microb. Rev.* 1:173–186 (1988).

Cheung and Ying, "Regulation of α– and β–Hemolysins by the sar Locus of *Staphylococcus aureus*," *J. Bacteriology* 176:580–585 (1994).

Cheung et al., "Insertional Inactivation of a Chromosomal Locus That Modulates Expression of Potential Virulence Determinants in *Staphylococcus aureus*," *J. Bacteriology* 177:3220–3226 (1995).

Cheung and Projan, "Cloning and Sequencing of sarA of *Stapohylococcus aureus*, a Gene Required for the Expression of agr," *J. Bacteriology* 176:4168–4172 (1994).

Cheung et al., "Regulation of exoprotein expression in *Staphylococcus aureus* by a locus (sar) distinct from agr," *Proc. Natl. Acad. Sci. USA* 89:6462–6466 (1992).

1: Compound 1 (10 µg/ml)
2: Compound 2 (20 µg/ml)
3: Compound 2 (10 µg/ml)
4: Compound 3 (5 µg/ml)
5: Compound 3 (2.5 µg/ml)

9: Clindamycin (0.5 µg/ml)
10: Ciprofloxacin (0.06 µg/ml)
11: Vancomycin (0.5 µg/ml)

Agr+: Agr+ supernatants
Agr-: Agr- supernatants
NC: Media (no cells)

SEQUENCE LISTING (1) GENERAL INFORMATION:

(iii) NUMBER OF SEQUENCES:    6

(2) INFORMATION FOR SEQ ID NO: 1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 1:

CGGGATCCAT AAAAATTACA ACTG     24

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 2:

ACGCGTCGAC GAATATTAAA ATTCCTTCAT TAC     33

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 3:

CGGGATCCTT TGTATTTAAT ATTTTAAC     28

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 4:

CGGGATCCGA TCTAGTTATA TTAAAAC     27

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

CCCTATGTGA TGTTTAGCTC     20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

TTAGGAGGTC TCGCTATGGA     20

INHIBITORS OF REGULATORY PATHWAYS

RELATED APPLICATIONS

The present application claims priority to U.S. Provisional Application Ser. No. 60/004,626, filed Sep. 29, 1995 (Bao et al., INHIBITORS OF REGULATORY PATHWAYS), which is incorporated herein by reference, including any drawings.

BACKGROUND OF THE INVENTION

This invention is related to the fields of antimicrobial agents and the treatment of microbial infections. It is, in addition, concerned with methods for identifying antimicrobial agents and agents which facilitate the action of antimicrobial agents.

None of the information presented below is admitted to be prior art to the pending claims, but is provided only to aid the understanding of the reader.

The traditional approach to treatment of microbial infections has largely been to treat with antibiotics which either kill the microbes (microcidal) or inhibit microbial growth. These antibiotics exert their antimicrobial action both in culture (in vitro), and in an infection (in vivo). Extensive screening by the pharmaceutical industry in the last fifty years for bactericidal and bacteriostatic compounds has led to the discovery and development of large numbers of antibiotics, most of which are members of a much smaller number of structural or functional classes. Examples of those classes of antibiotics are the β-lactams (which include the penicillins and cephalosporins), aminoglycosides, and glycopeptides.

However, an increasingly serious problem is the spread of broad antibiotic resistance, both geographically and in different microbial species. Antibiotic resistance is particularly notable in bacteria. Such bacterial resistance to an antibiotic(s) may be due to any of a number of mechanisms. For β-lactam resistance, an important mode is the production of β-lactamases. Other mechanisms which result in drug resistance include the development of altered antibiotic targets and reduced cellular uptake of the drug.

An example of the development of antibiotic resistance is the appearance of methicillin resistance in *Staphylococcus aureus*. Methicillin is a penicillinase-stable β-lactam antibiotic often used for the treatment of penicillinase-producing strains of *Staphylococcus aureus*. However, methicillin-resistant *S. aureus* (MRSA) have acquired a methicillin-insensitive cellular target which allows bacteria to grow in the presence of the drug, and the incidence of MRSA infections has become a serious problem (Chambers, *Clin. Microb. Rev.* 1:173–186, 1988; De Lencastre et al., *J. Antimicrob. Chemother.* 33:7–24, 1994). The current average incidence of MRSA in some, large hospitals in the USA increased from 8% in 1986 to 40% in 1992, and there are MRSA strains which are susceptible to only a single class of clinically available antibiotics, the glycopeptides. There is a need for the discovery of new efficient anti-MRSA drugs before resistance to glycopeptide antibiotics develops in multi-resistant MRSA strains.

The problems associated with antibiotic resistant bacteria are not limited to *S. aureus*, but are present in a large number of bacterial pathogens. Therefore, there is a need for the development of new types of antibacterial agents, including ones directed to new targets. Such new antibacterial agents will not only reduce the problems associated with treating infections involving resistant bacteria, but can also provide additional therapeutic options even for treating bacteria which are still susceptible to currently available antibacterial agents.

One approach to developing such new antibacterial agents is to target bacterial pathogenesis. The bacterial products related to pathogenesis are often termed "virulence factors". Virulence factors are those biological molecules produced by a pathogenic bacterium that are essential for survival in the host organism but are not necessarily essential in vitro (where survival is meant to connote entry, attachment, evasion of host immune system, nutrient acquisition, and any other molecular processes necessary for adaptation to the host environment). Since most screening for novel antibiotics has been performed in vitro, virulence factors remain unexploited targets for antibiotic discovery screens. Based on estimates from other pathogenic organisms, the number of such virulence genes in *Staphylococcus aureus* is estimated to be 50–100 (see, Groisman and Ochman, *Trends in Microbiol. Sci.* 2:289–294 (1994); Muhldorfer and Hacker, *Microb. Pathogenesis* 16:171–181 (1994)).

SUMMARY OF THE INVENTION

This invention provides a novel approach to treating microbial pathogenesis by the administration of small molecules (compounds) which alter the functioning of a microbial global regulator of pathogens. This invention recognizes that reducing or eliminating the production of exoproteins, toxins, or other factors related to bacterial pathogenesis by affecting the regulation of their synthesis and secretion, can greatly alter the course and effects of a bacterial infection. This treatment approach is distinct from most prior antimicrobial treatments which attempted to either kill the microbial cells, or directly prevent them from reproducing. The antimicrobial action of the compounds of such antimicrobial treatments is exerted both in vivo, in an infection, and in vitro, in a culture, unless some specific compensating factor(s) is provided which allows survival or growth in the presence of the antimicrobial agent. In contrast, this invention is directed at the global regulation of microbial factors which are involved in the pathogenesis process, but are not necessarily essential for microbial survival or growth in vitro.

Such pathogenesis factors are associated with specific microbial genes, which may encode a variety of different types of pathogenesis-related products. Such products may include, e.g., specific protein toxins and regulatory molecules which affect the production of other molecules such as toxins. The agr locus of *Staphylococcus aureus* is an example of a set of genes which encodes regulatory molecules which control the production of a large number of toxins and exoproteins, and enzymes. In particular, transcription of RNAIII from the P3 promoter is essential for the agr effect on the related exoproteins (see Detailed Description below), and is thus identified as a global pathogenesis gene regulator. Thus, inhibition of the production of RNAIII inhibits the agr effect, which includes both upregulation of certain products and down-regulation of other products. However, inhibition of other global regulators of pathogenes, whether in *Staphylococcus aureus* or in other bacterial species, has similar potential.

In this invention, small molecules have been identified that inhibit the naturally occurring, growth dependent induction of the P3-driven RNAIII and those downstream virulence factors under its influence. Such compounds, termed antipathogenics, may show some growth inhibitory activity at higher concentrations, but also show antipathogenic behavior at sub-MIC levels. (Antipathogenics refers to compounds which reduce the pathogenesis-related effects of one or more pathogenesis factors.) Therefore, treatment with such molecules has effects such as attenuating host inflammatory response, decreasing load of bacterial toxins, disfavoring colonization of the host by the bacteria, allowing the host to clear the infection, or potentiating the effect of traditional antibiotic drugs by weakening the bacteria or relocating them to a drug- or host factor-accessible compartment.

Therefore, in a first aspect, this invention provides methods of treating a bacterial infection of an animal, preferably of a mammal, specifically including in a human, by administering a compound which alters the activity of a global regulator of pathogenes. In a preferred embodiment, this is accomplished by inhibiting the level of activity of the global regulator, such as by inhibiting expression of that regulator by the administered compound. However, a compound which inhibits expression of a global regulator (or otherwise affects the level of activity of the regulator) need not act directly on that specific gene (or molecule). For instance, such an inhibitor can act at an upstream regulator, which directly or indirectly regulates expression of the global regulator. In a preferred embodiment, the compound inhibits the expression of RNAIII, or is active against the agr, xpr, sae, or sar genes or a homolog thereof.

In this context, the term "treating" refers to administering a pharmaceutical composition for prophylactic and/or therapeutic purposes. The term "prophylactic treatment" refers to treating a patient who is not yet infected but is susceptible to or otherwise at risk of a particular infection. The term "therapeutic treatment" refers to administering treatment to a patient already suffering from an infection.

The term "bacterial infection" refers to the invasion of the host animal (e.g., mammal) by pathogenic bacteria. This includes the excessive growth of bacteria which are normally present in or on the body of a mammal, but more generally, a bacterial infection can be any situation in which the presence of a bacterial population(s) is damaging to a host mammal. Thus, a mammal is suffering from a bacterial infection when excessive numbers of a bacterial population are present in or on a mammal's body, or when the effects of the presence of a bacterial population(s) is damaging the cells or other tissue of a mammal.

The terms "administering" and "administration" refer to a method of giving a dosage of an antibacterial pharmaceutical composition to a mammal where the method is, e.g., topical, oral, intravenous, transdermal, intraperitoneal, intramuscular, or intrathecal. The preferred method of administration can vary depending on various factors, e.g., the components of the pharmaceutical composition, the site of the potential or actual bacterial infection, the bacterium involved, and the severity of an actual bacterial infection.

By "comprising" it is meant including, but not limited to, whatever follows the word "comprising." Thus, use of the term "comprising" indicates that the listed elements are required or mandatory, but that other elements are optional and may or may not be present. By "consisting of" is meant including, and limited to whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "mammal" refers to any organism of the Class Mammalia of higher vertebrates that nourish their young with milk secreted by mammary glands, e.g., mouse, rat, and, in particular, human, dog, and cat.

In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells causing or contributing to a bacterial infection. The dose of antibacterial agent which is useful as a treatment is a "therapeutically effective amount." Thus, as used herein, a therapeutically effective amount means an amount of an antibacterial agent which produces the desired therapeutic effect as judged by clinical trial results and/or animal models of infection. This amount can be routinely determined by one skilled in the art and will vary depending upon several factors, such as the particular bacterial strain involved and the particular antibacterial agent used. This amount can further depend on the patient's height, weight, sex, age, and renal and liver function or other medical history. For these purposes, a therapeutic effect is one which relieves to some extent one or more of the symptoms of the infection and includes curing an infection.

As used in this disclosure the term "pathogenesis factor" or "virulence factor" refers to a molecule produced by an infecting organism which has a significant function in the bacterial infection process. This includes molecules which are involved in the adaptation of the bacteria to an animal (e.g., mammalian host), establishment of a bacterial infection, in the maintenance of a bacterial infection, and in producing the damaging effects of the infection to the host organism. Further, the term includes molecules which act directly on host tissue, as well as molecules which regulate the activity or production of other pathogenesis factors.

In *Staphylococcus aureus*, an "agr-related pathogenesis factor" is a molecule which is significantly linked with the expression of the operons of the agr locus. Thus, the term includes the specific toxins, proteases, and other pathogenesis factors regulated by the products of the agr locus, as well as both upstream and downstream regulatory molecules.

Another related term "pathogenesis genes" or "pathogenes" refers to a bacterial gene which encodes a pathogenesis factor, which includes genes which directly encode products such as proteases, as well as biosynthetic genes which encode a product which is directly involved in the synthesis of non-polypeptide molecules involved in pathogenesis. It further includes genes which encode regulatory molecules which affect the level of production of other molecules.

Some such regulatory molecules are termed "global regulators." While a regulatory molecule controls the level of expression of at least one other bacterial gene, to be termed a global regulator such a molecule should coordinately regulate the expression of several linked or unlinked genes to achieve a particular physiological adaptation of functional outcome. This does not mean that the global regulator exerts exclusive control over the level of expression of those other genes, but rather means that a change in the level of activity of the global regulator will significantly alter the level of expression of at least three other genes. A clear example of such a global regulator is the RNAIII transcript, which is transcribed from the P3 promoter of the agr locus in *Staphylococcus aureus*, and which affects the level of expression of numerous products, some of which are specified in the Description of the Preferred Embodiments below. Since numerous of the products regulated by the agr locus are pathogenesis factors, the agr locus is a global regulator of pathogenesis genes.

In the context of global regulators of pathogenesis genes, the term "homolog" refers to gene sequences from different bacterial strains or species which have significantly related nucleotide sequences, and consequently gene products which have significantly related nucleotide or amino acid sequences. Preferably, homologous gene sequences will have at least 50% sequence identity (as defined by the maximal base match in a computer-generated alignment of two nucleic acid sequences), more preferably at least 60%, and most preferably at least 80%. For polypeptide gene products of such homologous genes, generally the gene products also exhibit a significant degree of amino acid sequence identity. Thus, for such polypeptide products of homologous genes, the amino acid sequences have at least 25% sequence identity over a sequence of 100 or more amino acids, more preferably at least 40%, still more preferably at least 60%, and most preferably at least 80%. In addition, in the present context, the products of the homologous gene sequences are also involved in regulation of a cellular response.

In a further aspect, this invention provides methods of treating an infection involving a bacterium (e.g., S. aureus) by administering a compound which inhibits one or more pathogenesis factors modulated by agr, xpr, sar, or sae. Usually, but not necessarily, this involves reducing the production of those factors.

The term "modulated" means that the level of a pathogenesis factor in the in vivo environment can be altered by changes in the presence or concentration of a particular gene product. For example, the agr-related pathogenesis factors are modulated by RNAIII.

In a related aspect this invention also provides a method for prophylactic treatment of a mammal, in particular a human, in order to prevent a bacterial infection. Such treatment comprises administering an inhibitor of a global regulator to the mammal. Preferably such treatment would be used when the patient is at risk of contracting or developing a bacterial infection. Particular embodiments of this method are as described above for the method of treating a bacterial infection. Such a prophylactic treatment method may have particular benefit, for example, for treating patients prior to surgical operations.

In another related aspect, this invention provides pharmaceutical compositions having an inhibitor of a global pathogene regulator and a pharmaceutically acceptable carrier.

The specific screening hits described as Compounds 1–18 (FIGS. 6–8) are more generally described by the Structures 1–14, including the narrower descriptions of Structures 1A, 2A, 2B, 3A, 4A, 5A, 6A, 7A, 8A, 9A, 1A, 11A, 12A, 13A, and 14A (as shown in FIGS. 9–12), which also describe related compounds. Active related compounds can be obtained, for example, as commercially available analogs of previously identified hits, by synthesis, by modification of identified active compounds, and by identification of new screening hits. Thus, in preferred embodiments of the therapeutic compositions, methods of treating a bacterial infection, and methods of prophylactic treatment described herein, the inhibitor is an active compound described by one of Structures 1–2 and 4–14 or one of the corresponding narrower structure descriptions, Structures 1A, 2A, 2B, 4A, 5A, 6A, 7A, 8A, 9A, 10A, 11A, 12A, 13A, and 14A. For each of the general structures, the substituent groups (R or X groups) are as described in the Detailed Description below.

Likewise, in another related aspect, this invention provides pharmaceutical compositions having an inhibitor of a regulator related to agr, sar, sae, or xpr, or of one or more pathogenesis factors modulated by agr, sar, sae, or xpr, and a pharmaceutically acceptable carrier.

In a further aspect the invention provides screening methods for potential inhibitors of global regulators of bacterial pathogenes. In preferred embodiments, the amount of translation product resulting from a globally regulated promoter region/reporter gene hybrid construct is determined in the presence and absence of potential inhibitors. The DNA construct is incorporated into a bacterial cell which can induce transcription from the pathogenesis gene promoter in response to an environmental signal. A potential inhibitor is then a compound which reduces the level of, or eliminates, transcription of the hybrid DNA, and so eliminates, or reduces the amount of the translation product. In an embodiment where the reporter gene is a β-lactamase gene, the presence of the translation product can be detected by the ability of the bacterial cell culture to produce color change in chromogenic β-lactamase substrate, such as nitrocefin, or by selection and growth of cells on a cleavable β-lactam-containing medium.

Such a potential inhibitor may act at any point of a regulatory sequence which is either upstream of or at the specific promoter. In the case where the P3 promoter as described above is used, such upstream elements include at least the products of the agrABCD genes of the P2 operon but are not limited to those elements. Inhibitors that block the agr-mediated global regulation will prevent induction of the Agr-P3 promoter, as well as downstream toxins and degradative enzymes.

In addition, since the above methods of screening are suitable for both known and unknown compounds and compound libraries, the invention also provides novel inhibitors for global regulators of pathogenes, such as RNAIII, or of components of the agr effect in S. aureus besides RNAIII.

The identification of novel targets and therapeutic approaches provides a method for preparing therapeutic agents active on global regulators of pathogenesis genes. Thus, in a further aspect, the invention provides methods of making an antibacterial agent. The methods involve screening for the agent by measuring the ability of the agent to alter the level of activity of a global regulator of pathogenesis genes, and synthesizing the therapeutic agent in an amount sufficient to provide the agent in a therapeutically effective amount to a patient. In a preferred embodiment, the screening involves detecting the amount of transcriptional or translational product from a hybrid DNA construct inserted in a cell, for cells grown in the presence and absence of the agent. The construct includes a regulatory region of a gene encoding a global regulator of pathogenesis genes, transcriptionally linked with a reporter gene.

Also in preferred embodiments, the global regulator is from a Staphylococcal strain, for example, the regulator can be encoded by a gene of the agr locus, xpr, sar, or sae. In particular preferred embodiments, the agent has a structure which is one of the structures described herein, e.g., Structures 1, 2, 4, 5, 6, 7, 8, 9, 10, 11, 12, 13, or 14. Further, the method can include the step of adding a pharmaceutically acceptable carrier to the agent.

Other features and advantages of this invention will be apparent from the following description of the preferred embodiments thereof, and from the claims.

In response to environmental or endogenously produced signals like the AgrBD-derived octapeptide, this two-component system transduces a signal that results in the transcription of promoters P2 and P3. The RNAIII produced from the P3 promoter has been shown to be a global regulator of many exoprotein genes, and is the basis for the exemplary screen described herein. The screen looks for inhibitors of this kind of regulatory cascade. Other global regulators exist (Sar, Xpr, Sae, etc) that may contribute to expression patterns of these exoproteins and other genes.

Figure 2:
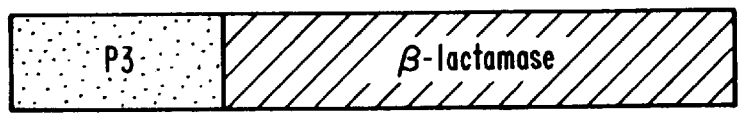

FIG. 2. Schematic of the P3-β-lactamase fusion. The basis for the exemplary screen is a fusion construct between the P3 promoter and a reporter gene (in this case, a β-lactamase). The production of RNAIII is critical in regulating downstream exoproteins. Fusion of the P3 promoter with an easily assayed reporter allows convenient monitoring of the effect of a given compound on RNAIII production.

Figure 3:
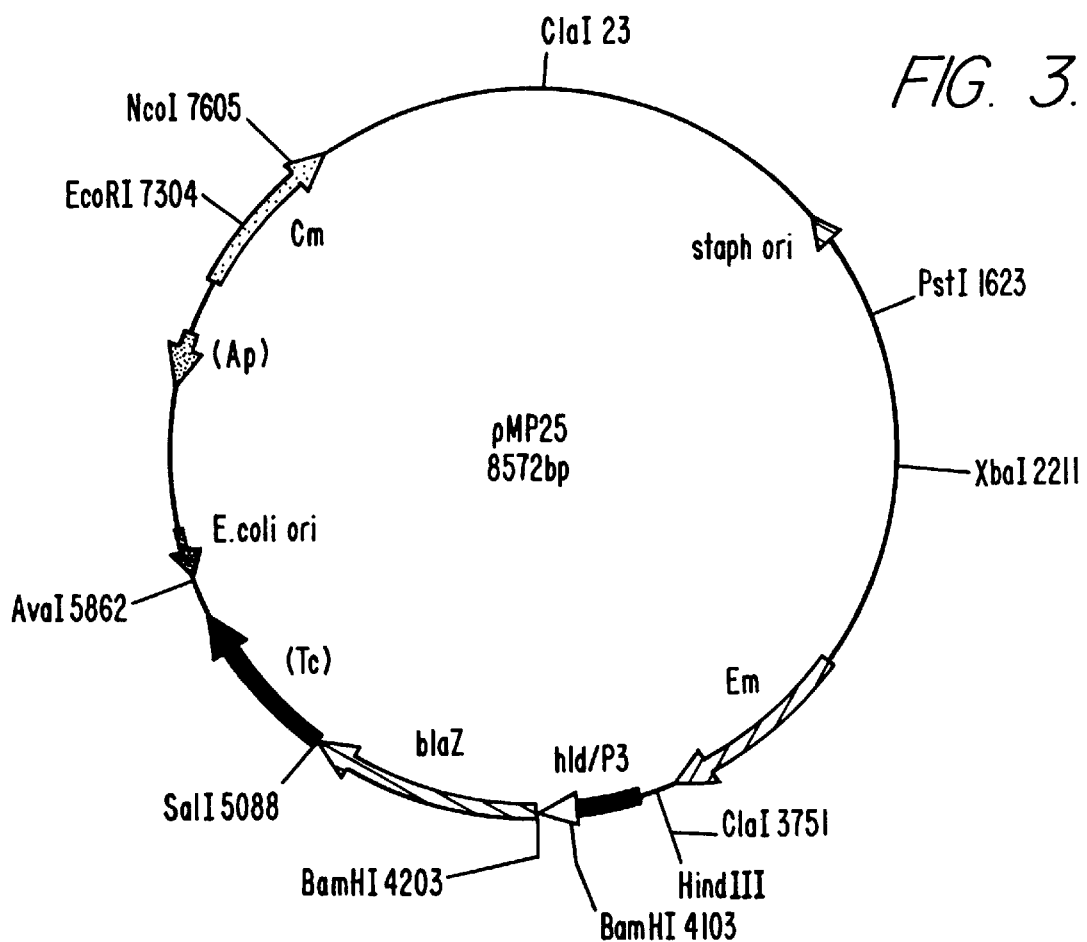

FIG. 3. The fusion construct is contained in the shuttle plasmid shown, which contains both an *E. coli* and an *S. aureus* origin of replication. The plasmid can be maintained with any of several selective agents, as it contains resistance determinants to erythromycin and chloramphenicol.

Figure 4:
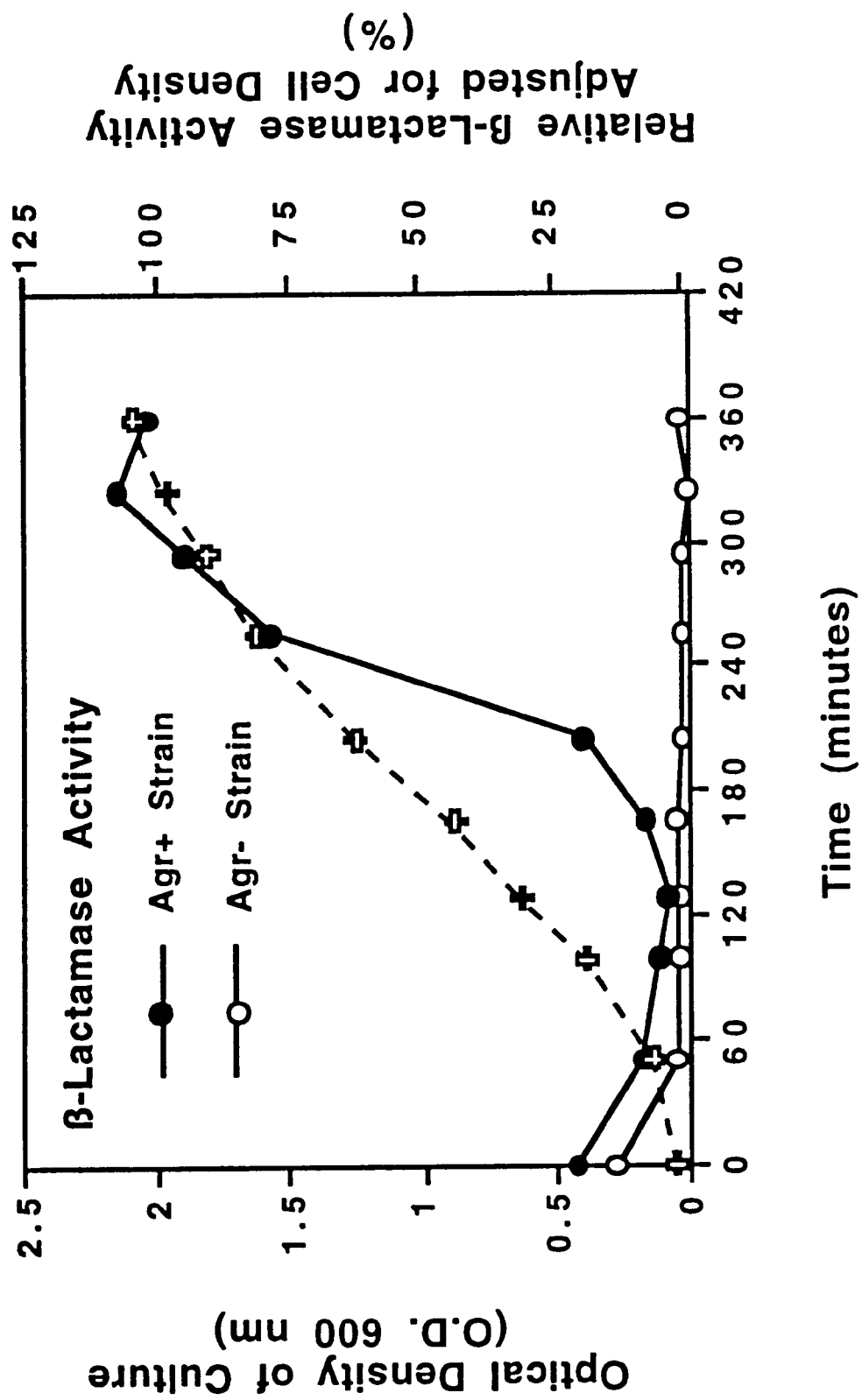

FIG. 4. Graph of the temporal regulation and Agr ependence of the P3-driven β-lactamase activity. The lasmid shown in FIG. 3 shows the expected phenotypes in Agr= and Agr− host cells. Lacking key components of the Agr operon, the fusion is inert in the Agr− cells and little or no β-lactamase activity is detected. By contrast, as has been previously seen with RNAIII in Agr+ cells, the P3 promoter becomes active in mid-log phase, as evidenced by the sharp increase in β-lactamase activity.

Figure 5A:
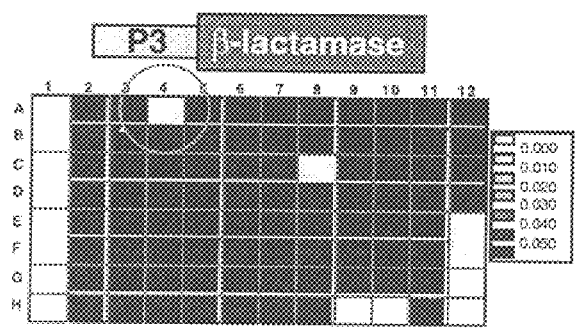
Figure 5B:
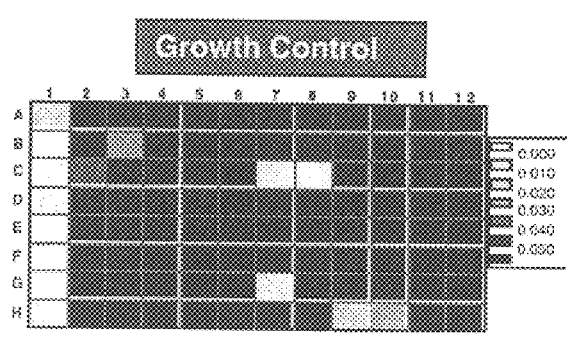

FIG. 5. Schematic example of the screen assay plates. Certain compounds of interest will affect the production of beta-lactamase without killing the cells. In the "growth control" plate, the fusion-containing Agr+ cells are tested with 80 different compounds in wells A2-H11. Columns 1 and 12 are devoted to controls as described in the text. After suitable exposure to compound, cell density is measured (O.D. 600 nm) and an aliquot is transferred to "P3-β-lactamase" assay plate for testing the activity of the reporter enzyme by a nitrocefin assay (O.D.490 nm). Compounds are evaluated using the algorithms shown below. "Active" compounds may be acting to prevent P3 induction. Alternative hypotheses are explored in secondary assays.

SCREEN ALGORITHMS:

Growth in presence of test compounds:

$$[(T650-B650) \div (C650-B650)] \times 100 = \%\text{ of growth in presence of test compound}$$

T650: Average growth of cells (8325-4/pMP25) with test compound (O.D. at 650 nm)

B650: Average media blank controls (O.D. at 650 nm)

C650: Average growth of control cells (8325-4/pMP25) without compound (O.D. at 650 nm)

If score is <70%: Indicates a "growth inhibitor" and compound is considered "inactive".

If score is 70–80%: Indicates a "growth retardant (GR)" and compound is considered a potential "active" hit.

If score is ≧80%: Indicates a potential "active" hit.

Inhibition of β-lactamase activity:

$$(\{[(T490-B490) \div (T650-B650)] \div [(C490-B490) \div (C650-B650)]\} - 1) \times -100 = \%\text{ inhibition of }\beta\text{-lactamase activity due to test compound and corrected for cell density}$$

T650: Average growth of cells (8325-4/pMP25) with test compound (O.D. at 650 nm)

B650: Average media blank controls (O.D. at 650 nm)

C650: Average growth of control cells (8325-4/pMP25) without compound (O.D. at 650 nm)

T490: Average activity of β-lactamase in cells exposed to test compound (O.D. at 490 nm)

B490: Average media and buffer blank controls (O.D. at 490 nm)

C490: Average activity of β-lactamase in untreated control cells (O.D. at 490 nm)

If score is ≧75%: Indicates an "active" compound (i.e., potential inhibitor of the Agr system if not directly inhibiting the reporter enzyme).

If score is <75%: Indicates an "inactive" compound (compound is rejected).

If score is ≦−25%: Indicates an "Inducer" (i.e., potential inducer of the Agr system).

Figure 6:
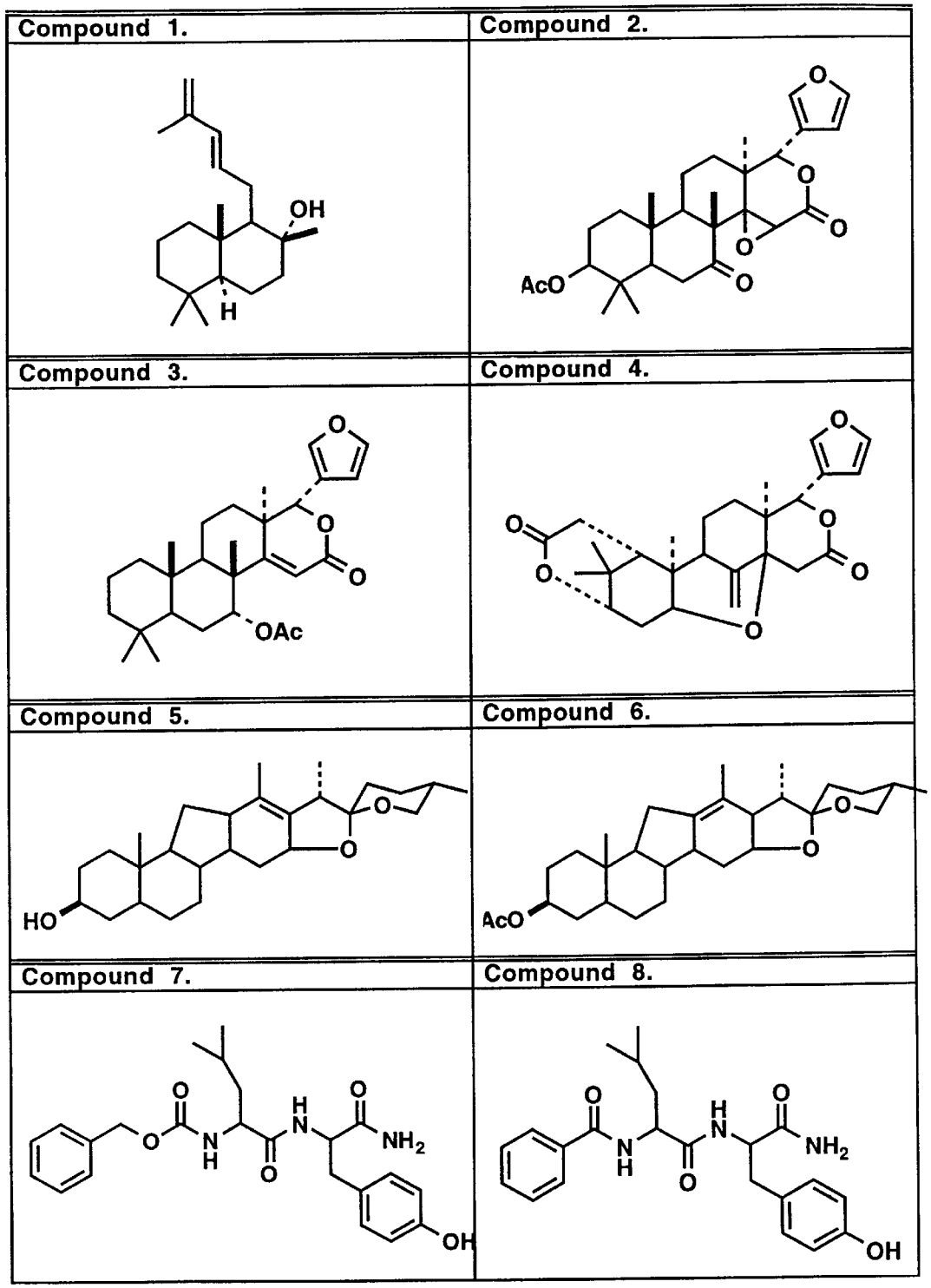
Figure 7:
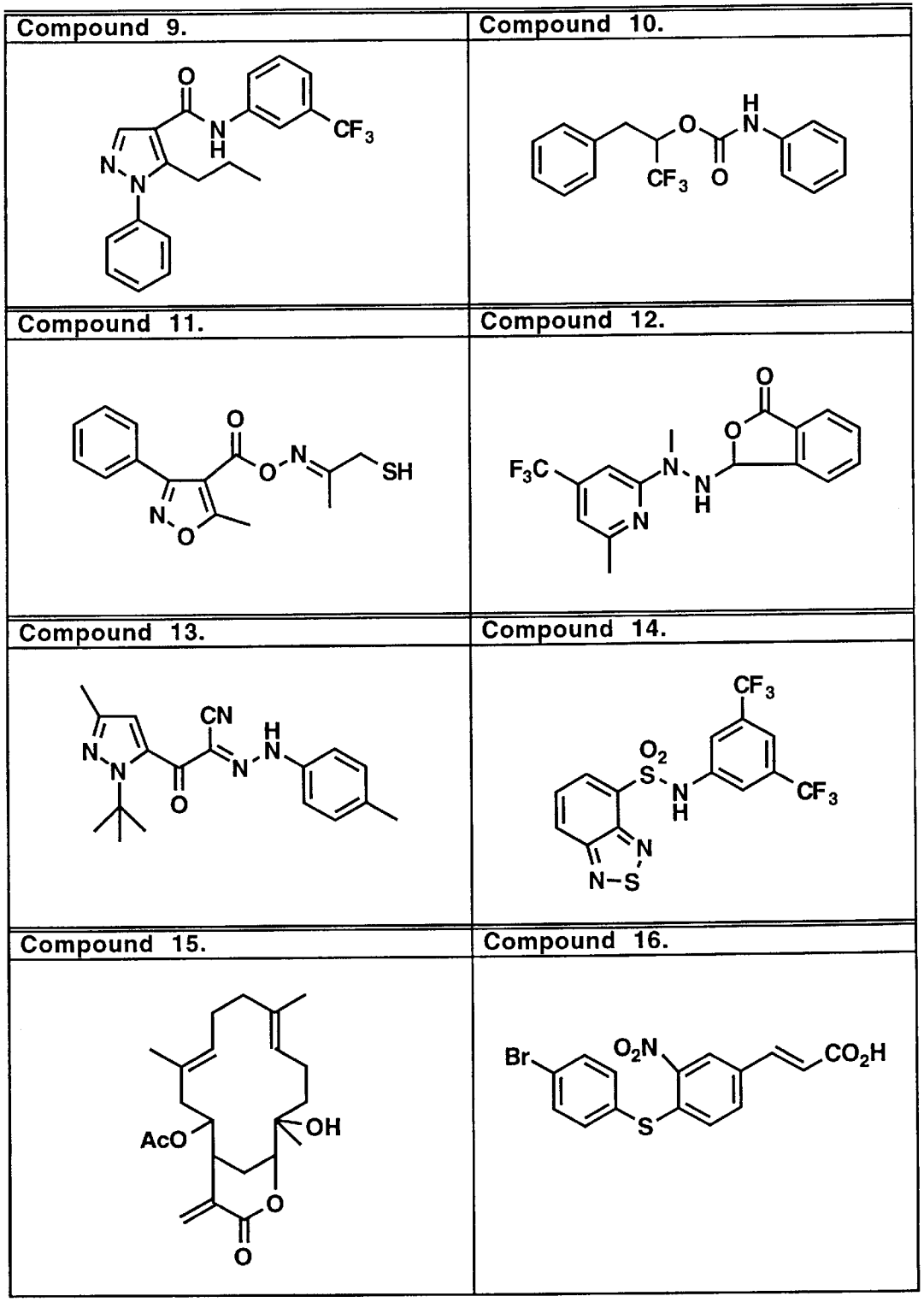
Figure 8:
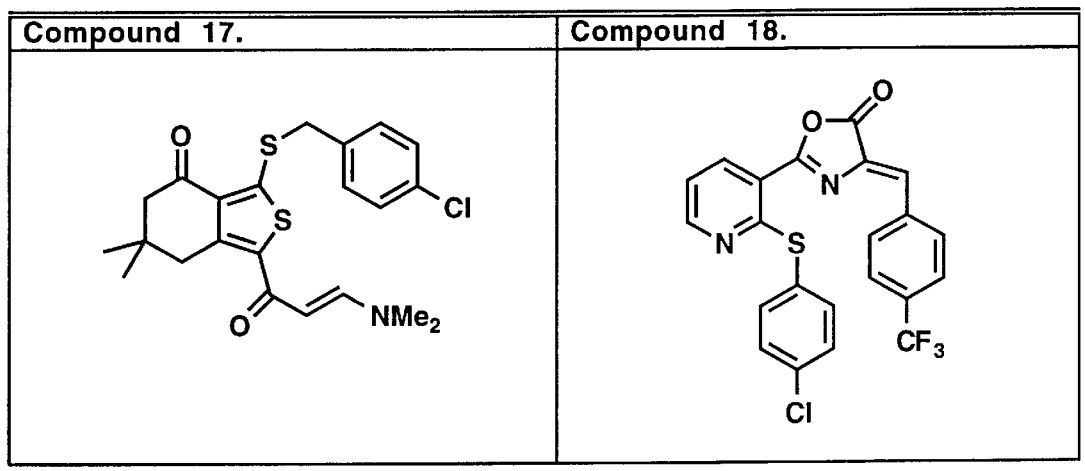
Figure 9:
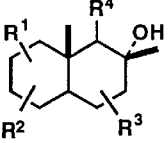
Figure 10:
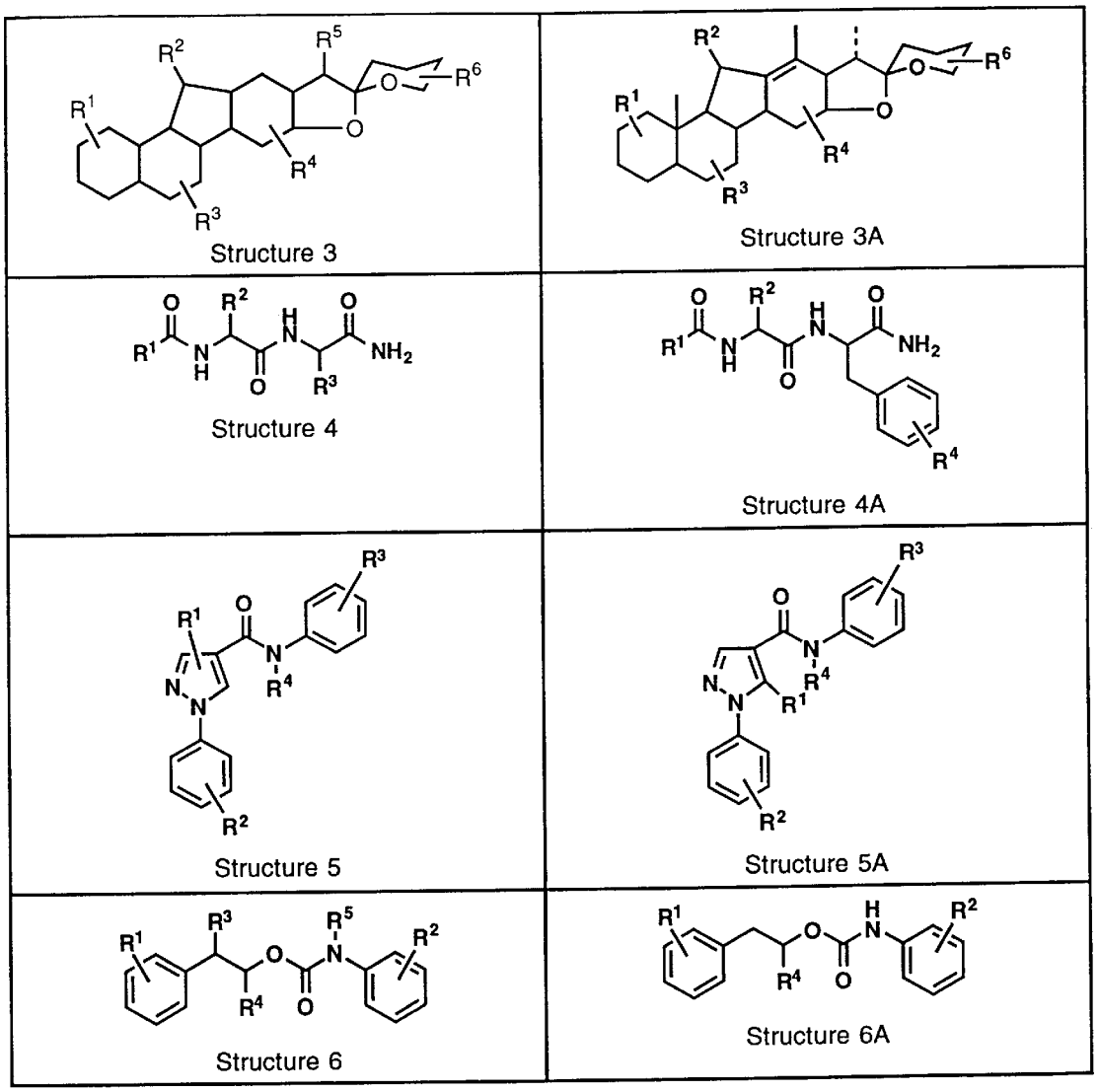
Figure 11:
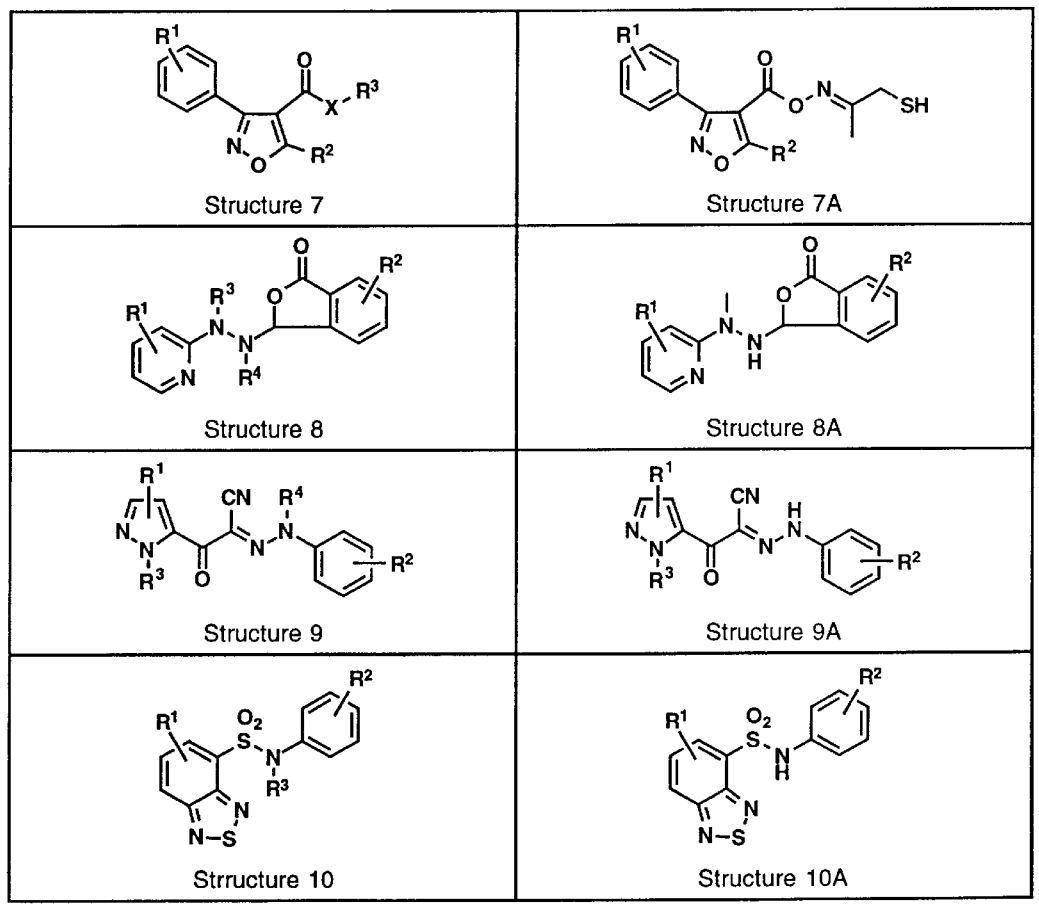
Figure 12:
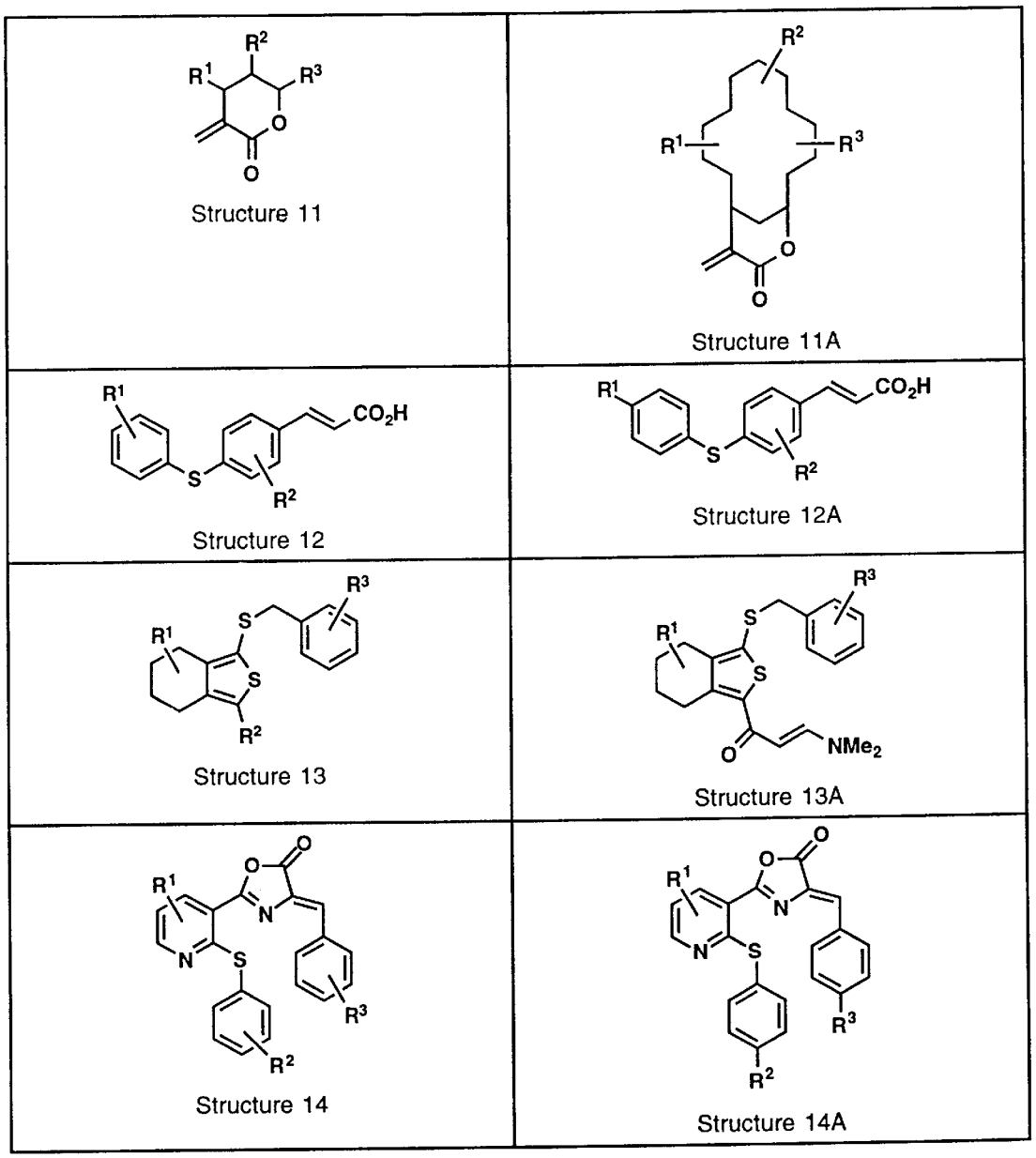

FIGS. 6–8. Chemical structures of confirmed screen hits (Compounds 1–18) identified using the P3-β-lactamase fusion screen.

FIGS. 9–12. Generic and sub-generic structures describing Compounds 1–18 (screen hits) and related compounds. Each generic structure is designated by a number, and the corresponding sub-generic structure(s) is designated by the same number followed by a letter. The table below shows the correspondence between the specific screening hits (Compounds 1–18) and the generic and sub-generic structures.

TABLE 1

Correspondence of Screening Hit Compounds, Generic Structures, and Sub-generic Structures

| Compound No. | Generic Structure No. | Sub-generic Structure No. |
|---|---|---|
| 1 | 1 | 1A |
| 2 | 2 | 2A |
| 3 | | |
| 4 | | 2B |
| 5 | 3 | 3A |
| 6 | | |
| 7 | 4 | 4A |
| 8 | | |
| 9 | 5 | 5A |
| 10 | 6 | 6A |
| 11 | 7 | 7A |
| 12 | 8 | 8A |
| 13 | 9 | 9A |
| 14 | 10 | 10A |
| 15 | 11 | 11A |
| 16 | 12 | 12A |
| 17 | 13 | 13A |
| 18 | 14 | 14A |

Figure 13A:
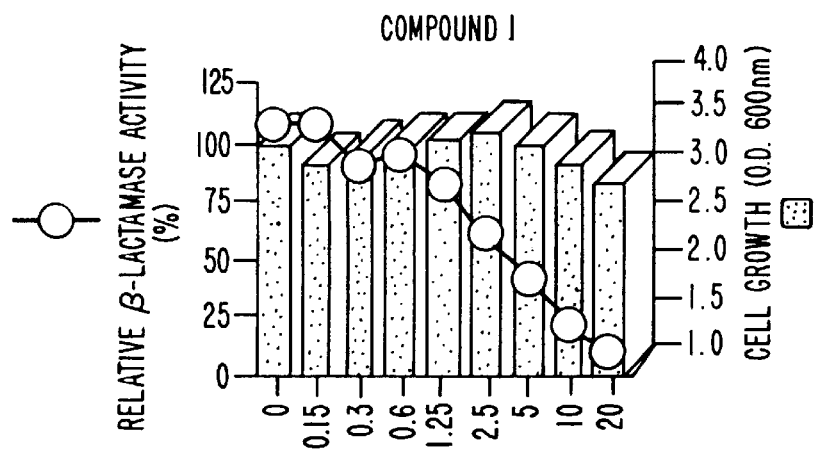
Figure 13B:
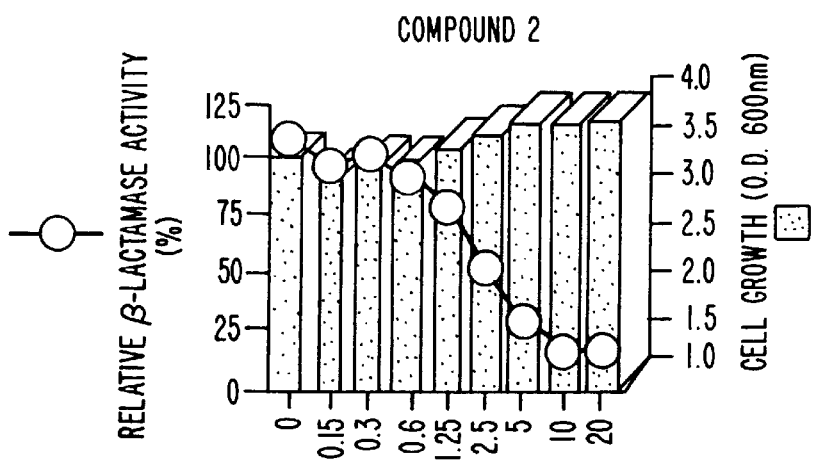
Figure 13C:
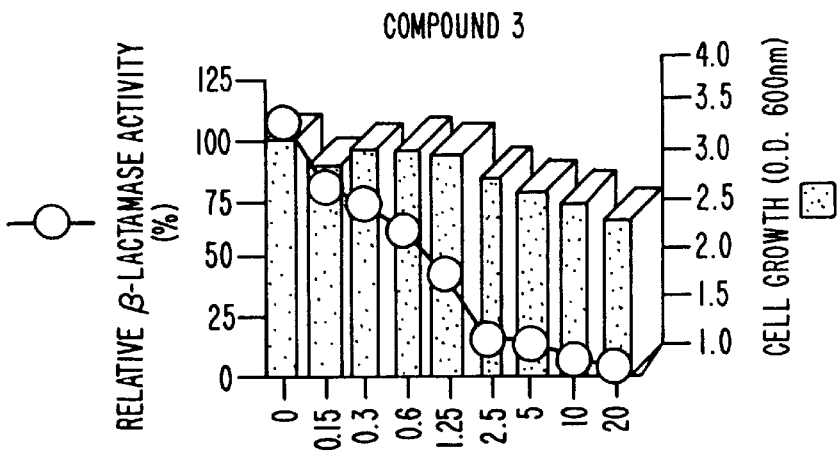

FIG. 13. Dose-Response curve for three of the active compounds. Note that, even at concentrations that do not appreciably alter growth, the compounds markedly reduce the P3-driven output of β-lactamase. It is also noteworthy that the dose response and growth characteristics are distinct for these three compounds.

Figure 14:
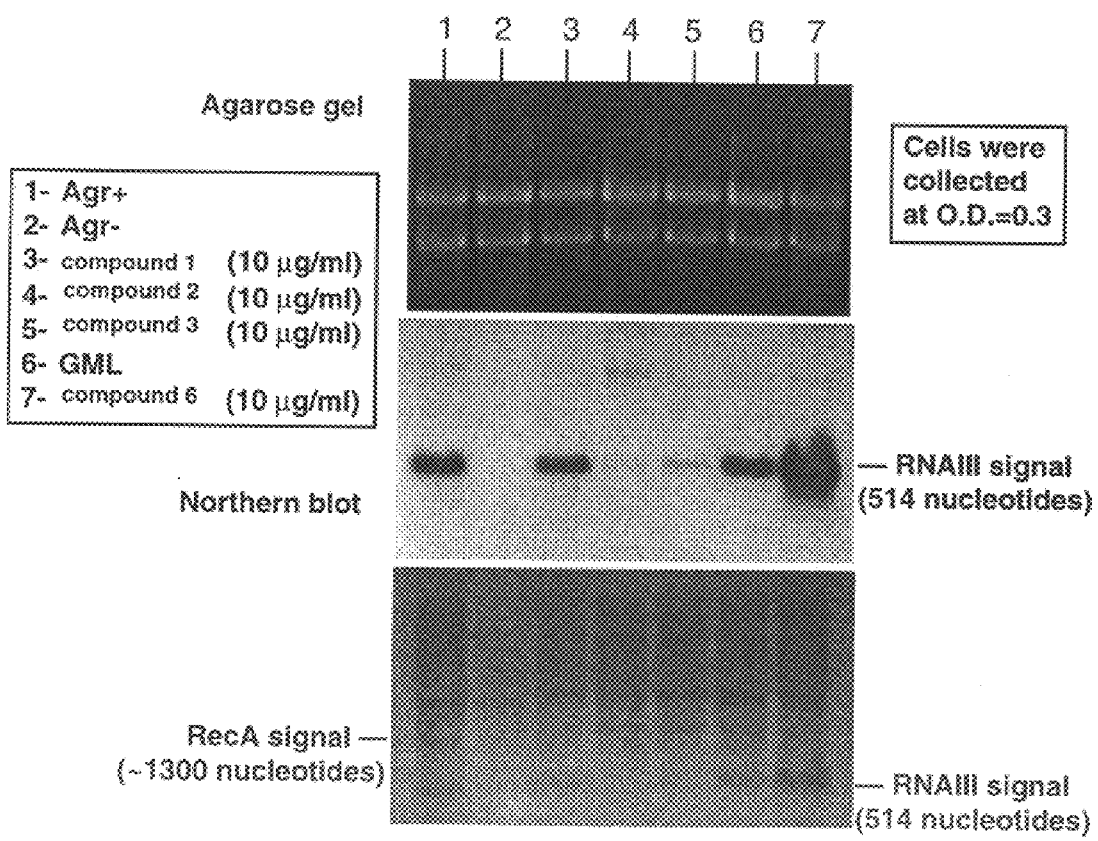

FIG. 14. Northern Blots for RNAIII and for RecA (control). A more direct assay of the effect of active compounds on the P3 promoter activity is performed on confirmed hits. Total RNA is isolated from treated and untreated cells when cultures reach similar density (O.D. 600 nm). The RNA is probed on a Northern Blot with a RNAIII-specific probe (see text) or, as a control for total RNA, with a RecA-specific probe. Lane 1, Agr+. Lane 2, Agr–. Lanes 3–5, Agr+ treated with different active compounds. The Northern Blot shows varying levels of reduction of RNAIII expression caused by the three active compounds. Glycerol monolaureate (GML) has no effect on RNAIII production (lane 6). Note that lane 7 shows a marked increase in RNAIII, because it contains RNA derived from cells treated with compound 6 that is considered a P3-inducer (as estimated by the increased activity of the β-lactamase reporter and the screen algorithms). The results shown here indicate the validity of the reporter system for monitoring up-regulation as well as down-regulation of the Agr operon.

Figure 15:
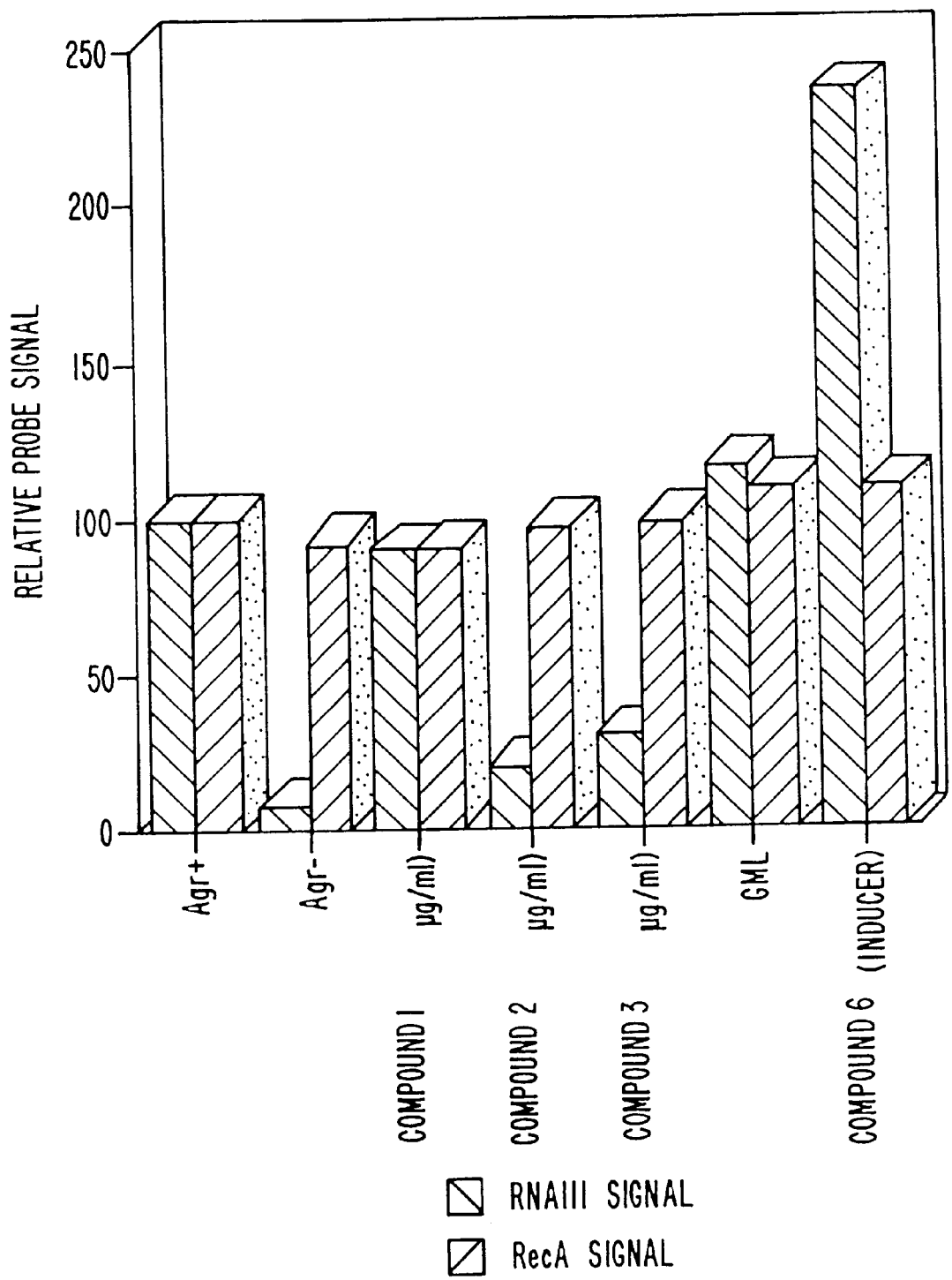
Figure 16:
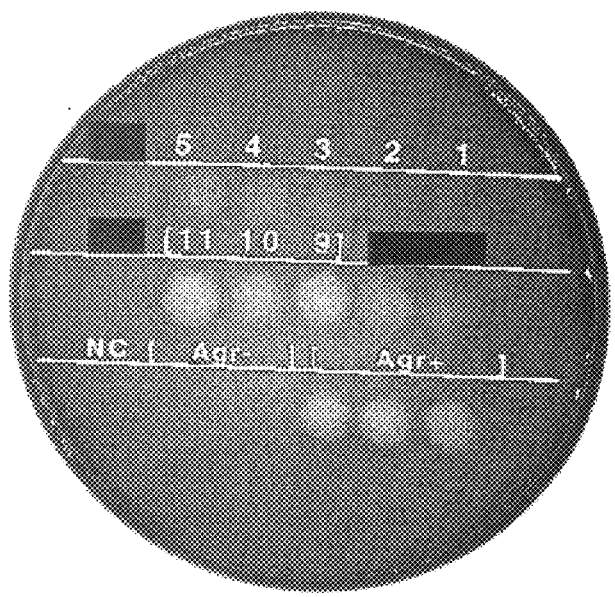

FIG. 15. Quantitation of Northern Blot from FIG. 14. Probes were labeled in a manner that allowed chemiluminescent detection. This was captured on phosphor screens and quantitated with a Molecular Imager (BioRad), or autoradiograms were photographed and quantitated using a program in the public domain FIG. 16. Plate test for alpha-hemolysin. Supernatants of bacterial cell cultures grown in the presence of some active compounds identified in the screen were spotted onto a rabbit blood-agar plate containing 1 μg/ml ciprofloxacin to prevent bacterial grown on plates and allowed to incubate overnight at 35° C. Clearing is an indication of alpha-hemolysin activity, and opacity indicates inhibition or lack of hemolysin activity. Note that sub-MIC concentrations of active compounds inhibited alpha-hemolysin activity, while sub-MIC concentrations of traditional drugs like clindamycin, ciprofloxacin, or vancomycin did not inhibit alpha-hemolysin activity. Supernatants from untreated Agr+ and Agr– cultures were also spotted as controls. NC: No cell culture control (cultivation media). Note that all supernatants were corrected for cell density of individual cultures before spotting identical volumes on the plate.

Figure 17:
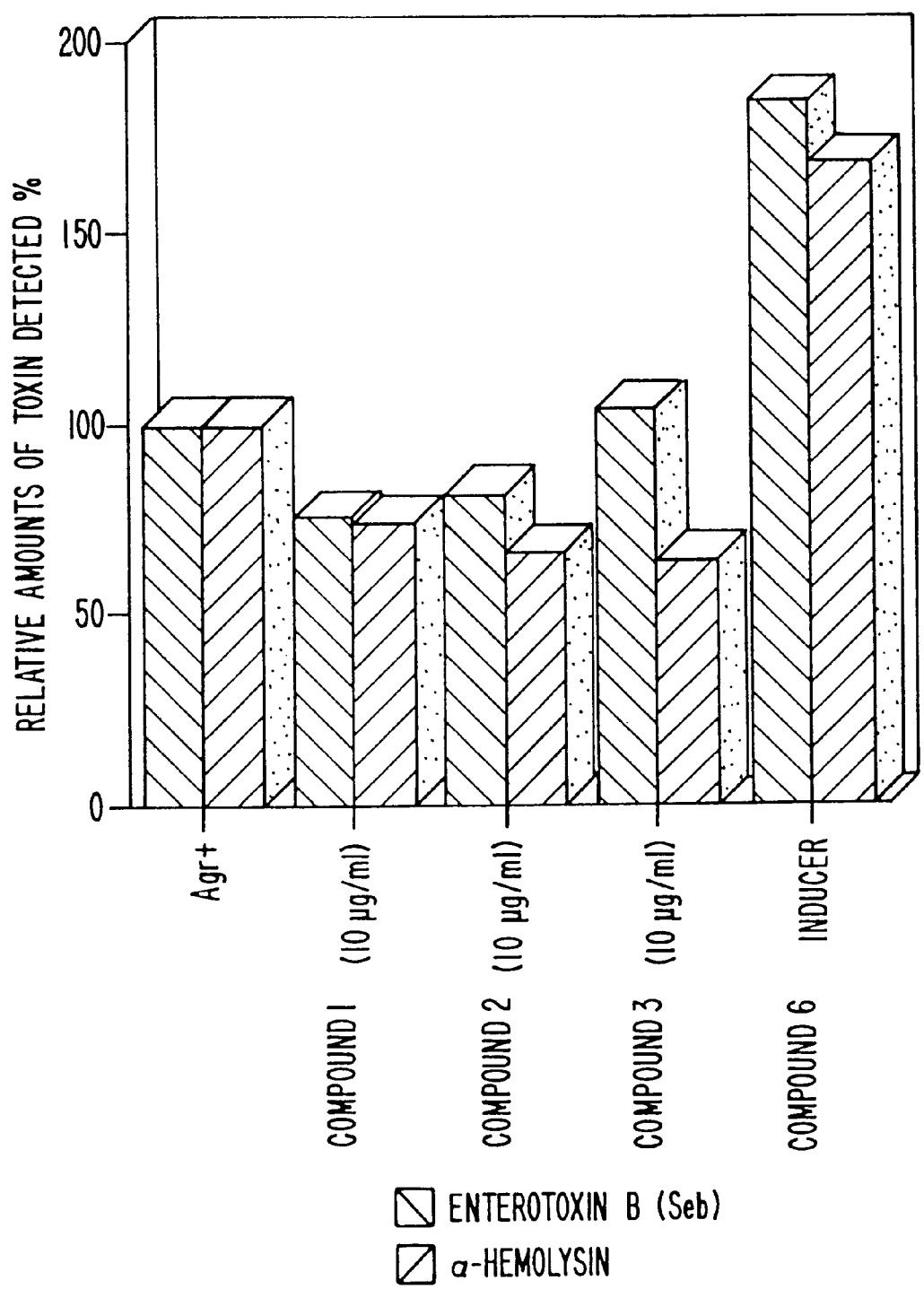

FIG. 17. Immunodetection and quantitation of staphylococcal enterotoxin B (Seb) and alpha-hemolysin in treated and untreated cultures. Exoproducts from treated and untreated cultures were assayed by dot blot using a specific anti-Seb or anti-alpha-hemolysin antibody and a second antibody that allowed chemiluminescent detection of immune complexes. The chemiluminescence was captured on phosphor screens and quantitated with a Molecular Imager (BioRad).

Figure 18:
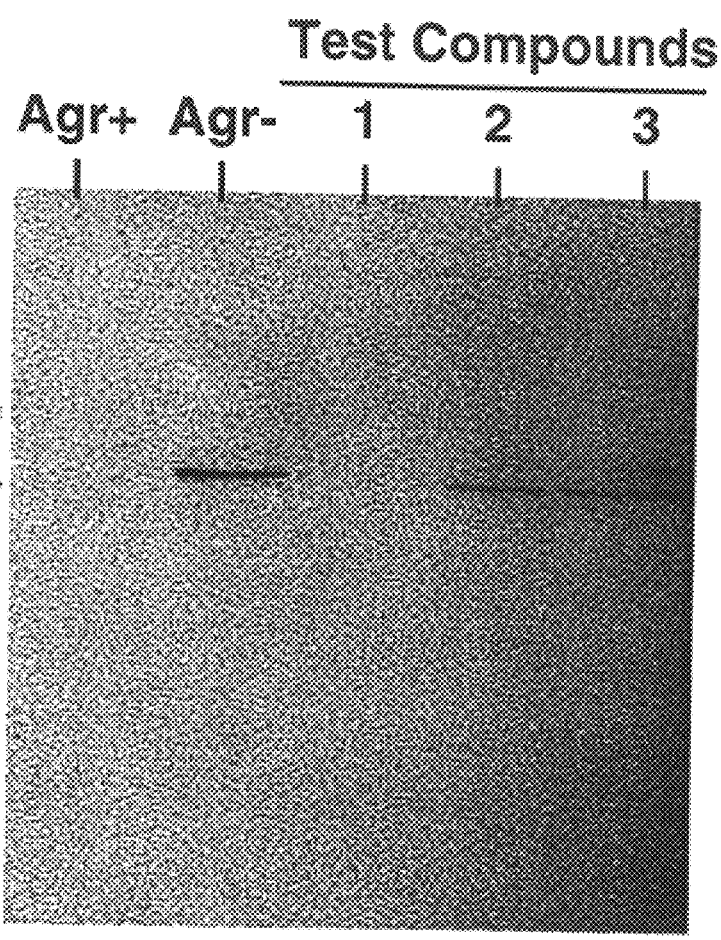

FIG. 18. Immunodetection of staphylococcal protein A in treated and untreated cultures. Cells were grown in presence of compounds 1, 2, or 3 to a similar density (O.D. 600 nm—0.5–0.6). Cells were lysed using lysostaphin prior to separation of cell surface proteins by SDS-PAGE. After electrophoretic transfer of proteins from the gel onto a nitrocellulose membrane, detection of protein A on the blot was possible by using a specific anti-protein A antibody and a second antibody that allowed chemiluminescent detection of immune complexes. The chemiluminescence was captured by autoradiography.

Figure 19:
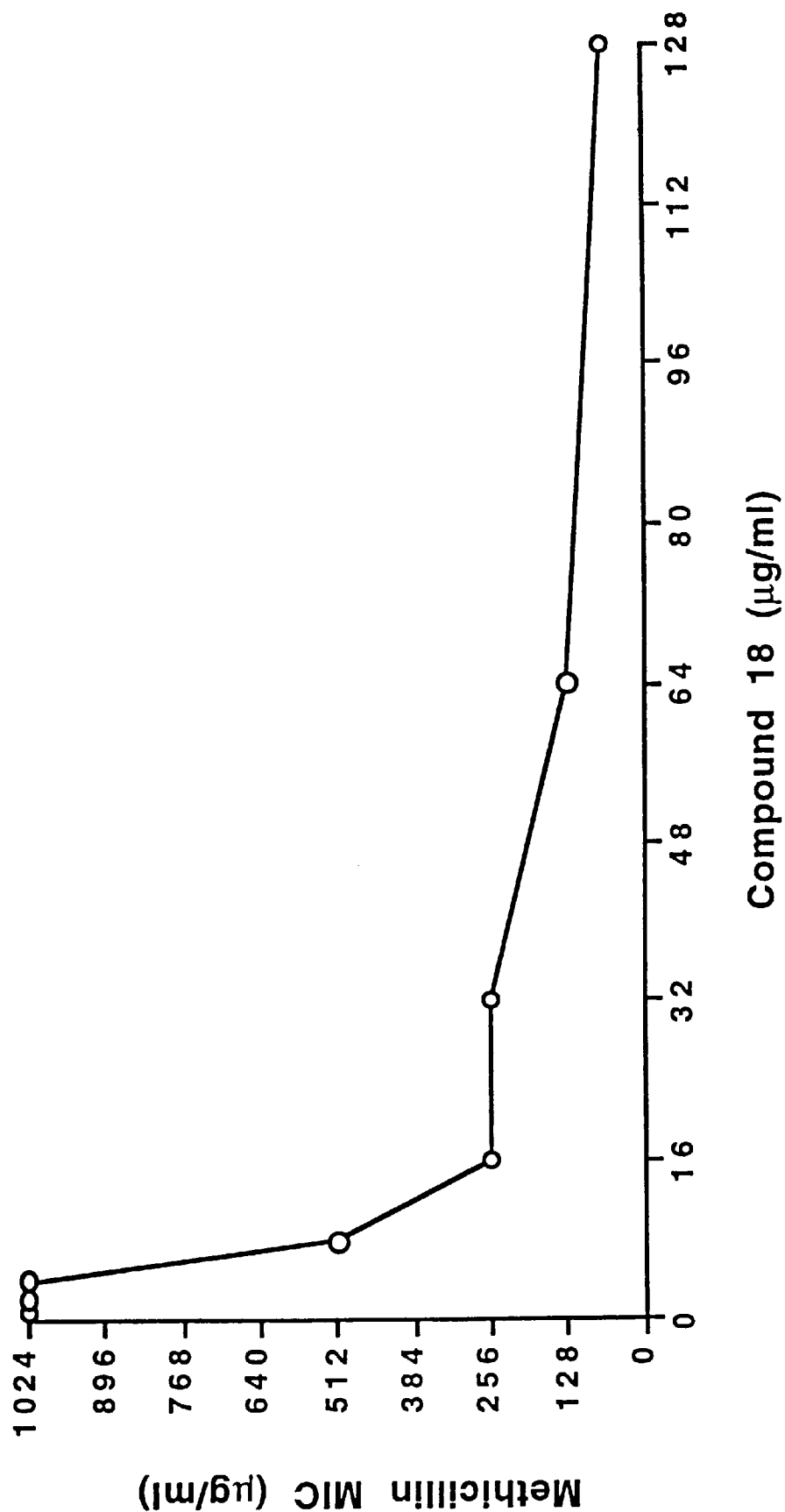

FIG. 19. Synergistic effect of compound 18 in combination with methicillin against a methicillin-resistant PBP 2a-producing strain of S. aureus (MRSA COL). Compounds were combined in a checkerboard assay performed in a microtiter plate in which a two dimensional matrix of the two compounds was created such that both compounds vary in concentration (see text). The minimal inhibitory concentration (MIC) of methicillin (the smallest concentration of methicillin that prevented visible growth of MRSA COL) was recorded for each test compound concentration.

Figure 20:
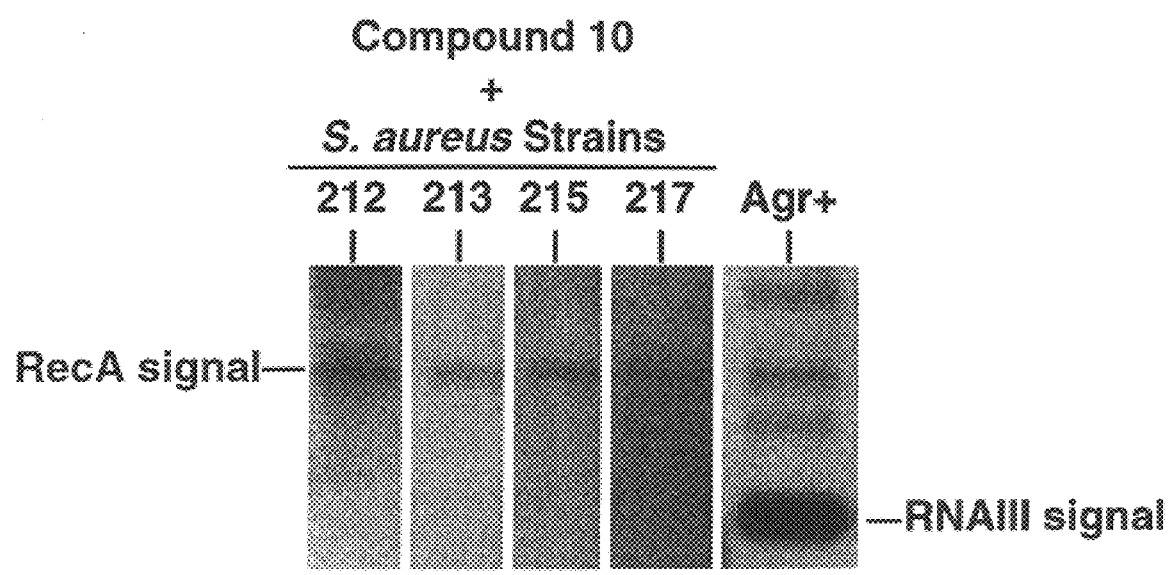

FIG. 20. Northern Blots for RNAIII detection in several clinical strains of S. aureus (no. 212, 213, 215, and 217) grown in the presence of Compound 10. Untreated strain 8325-4 (Agr+) is also represented and acts as a control to show the maximal amounts of RNAIII also detected in all clinical strains grown without the test compound. Total RNA was isolated from treated and untreated cells when cultures reach similar density (O.D. 600 nm). The RNA was probed on the Northern Blot with a RNAIII-specific probe or, as a control for total RNA, with a RecA-specific probe.

DESCRIPTION OF THE PREFERRED EMBODIMENTS

A. Pathogenesis Approach

An alternative, or supplemental approach to traditional antibiotic therapy is to treat the pathogenesis, altering the conditions or processes which make the presence of the bacteria damaging to the host organism. The appropriateness of this approach is seen by recognizing that a large number of genes are essential for establishing an infection and for producing molecules which cause the damage to the host organism. A exemplary, clinically significant organism for which considerable information on pathogenesis-related gene products and the regulation of those products is available is *Staphylococcus aureus*.

*Staphylococcus aureus* synthesizes a large number of extracellular proteins that are important during pathogenesis. These include several cytolytic toxins (α-, β-, γ-, and δ-hemolysin), toxic shock syndrome toxin-1 (TSST-1), enterotoxins, leucocidin, the immunoglobulin binding protein A, coagulase which activates prothrombin, several hydrolytic enzymes, and others (Smith, The initiation of sporulation, pp. 185–210, In I. Smith et al. eds., Regulation of procaryotic development, American Society for Microbiology, Washington, D.C. (1989)). In S. aureus, as in most other bacteria, pathogenicity is multifactorial, and the genes that encode the virulence factors are often subject to coordinate regulation. These regulating systems respond to changes in the bacterial environment during the process of infection and adapt the expression of the virulence genes in an appropriate manner. In laboratory cultures, the majority of extracellular proteins from S. aureus are produced preferentially at the end of the exponential phase of growth (Abbas-Ali and Coleman, 1977, *J. Gen. Microbiol.* 99:277–282).

Several mutations with a pleiotropic effect on the production of this group of extracellular proteins have been described (Yoshikawa et al., 1974, *J. Bacteriol.* 119:117–122; Bjorklind and Arvidson, 1980, *FEMS Lett.* 7:203–206). One such mutation is a Tn551 insertion in a locus designated agr (Recsei et al., *Mol. Gen. Genet.* 202:58–61 (1986)), for Accessory Gene Regulator.

B. General Features of Agr

Strains of S. aureus containing the above agr mutation show a decreased production of α-hemolysin, β-hemolysin, δ-hemolysin, TSST-1, enterotoxin B, epidermolytic toxins A and B, leucocidin, staphylokinase, nuclease, serine- and metallo-protease, and acid phosphatase, whereas the production of certain other exoproteins including protein A and coagulase is increased as compared to the isogenic parental strain (O'Toole and Foster, 1986, *Microb. Pathog.*

1:583–594; O'Toole and Foster, 1987, *J. Bacteriol.* 169:3910–3915; Recsei et al., *Mol. Gen. Genet.* 202:58–61 (1986); Gaskill et al., 1988, *J. Biol. Chem.* 263:6276–6280; Janzon et al., *Mol. Gen. Genet.* 219:480–485 (1989)). Thus, in general, agr+ strains show late log to post-exponential induction of a set of secreted proteins, and repression of some surface proteins as compared to agr– strains.

The Tn551 insertional mutation mentioned above has been localized to an open reading frame (ORF) encoding a 241 amino acid polypeptide (Peng et al., *J. Bacteriol.* 170:4365–4372 (1988)). This ORF, which is called agrA, is part of a polycistronic mRNA of approximately 3 kb which contains three additional ORFs, agrB, agrC and agrD (Janzon et al., *Mol. Gen. Genet.* 219:480–485 (1989); Novick et al., *EMBO J.* 12:3967–3975 (1993); Novick et al., *Mol. Gen. Genet.* 248:446–458 (1995)), which are also involved in the regulation of exoprotein synthesis.

Thus, the agr system provides a global regulator of pathogenesis (virulence) factors. As indicated above, agr encodes part of a regulatory cascade that controls expression of a large number of toxins and degradative enzymes that are produced during Staphylococcal pathogenesis (Peng et al., *J. Bacteriol.* 170:4365–4372 (1988); Janzon and Arvidson, *EMBO J.* 9:1391–1399 (1990); Novick et al., *Mol. Gen. Genet.* 248:446–458 (1995)).

The centerpiece of this regulation is a two-component regulatory system involved in signal transduction. AgrA and AgrC comprise a two-component regulatory system with features common to many bacteria (Parkinson and Kofoid, *Ann. Rev. Genet.* 26:71–112 (1992); Stock et al., *Micro. Revs.* 53:450–490 (1989)) and which show cross-species homology (Vandenesch et al., *FEMS Lett.* 111:115–122 (1993); Novick et al., *Mol. Gen. Genet.* 248:446–458 (1995)). Such systems contain a histidine kinase sensor/transmitter protein capable of sensing an environmental signal, autophosphorylation, and phosphotransfer, in addition to a response regulator protein that not only becomes phosphorylated by the histidine kinase, but is also instrumental in directly or indirectly regulating specific gene expression as a result of this phosphorylation. In their 1992 review, Parkinson and Kofoid cite more than 50 response regulators and more than 30 sensor/transmitters from at least 35 different bacteria (Parkinson and Kofoid, *Annu. Rev. Genet.* 26:71–112 (1992)). Most of these, including the Agr transmitter and receiver (at that time called AgrORF2 and AgrA), contain a canonical set of conserved residues and are termed orthodox transmitters or receivers. A notable exception is the AlgR2 gene product, involved in alginate regulation in *Pseudomonas aeruginosa*, which lacks or does not preserve certain sections conserved in the orthodox set.

The AgrA and AgrC proteins are the putative signal transduction proteins that allow induction of the Agr P2 and P3 promoters in response to the bacterial environment (Kornblum et al., Agr: a polycistronic locus regulating exoprotein synthesis in *Staphylococcus aureus*, pp. 373–402, In R. P. Novick (ed.), Molecular Biology of the Staphylococci, VCH Publishers, Inc., New York (1990)). Transcription of the agr operon is activated at the end of the exponential growth phase by an agrAC-dependent mechanism (Peng et al., *J. Bacteriol.* 170:4365–4372 (1988); Novick et al., *Mol. Gen. Genet.* 248:446–458 (1995)). Cloned agrA was shown to complement the pleiotropic exoprotein defect seen with such mutations as Tn551 (Novick et al., *EMBO J.* 12:3967–3975 (1993)) which are located within agrA, but not phenotypically similar mutations located elsewhere in the agr locus. In more detail, recent publications (Guangyong et al. *Proc. Natl. Acad. Sci. USA.* 92:12055–12059 (1995); Balaban and Novick, *Proc. Natl. Acad. Sci. USA*, 92:1619–1623 (1995)) showed that a peptidic factor produced by *S. aureus* accumulates during growth and is responsible for activating the Agr response. This autocrine regulation of toxin production by *S. aureus* is mediated by an octapeptide derived by AgrB and AgrD. AgrC serves as the cell surface receptor for the AgrBD-derived octapeptide and subsequently activates AgrA by signal transduction. These studies indicate that *S. aureus* virulence is regulated by a density-sensing system which is homologous to other bacterial regulatory system autoinduced by homoserine lactones. Furthermore, the organization of the *S. aureus* system resembles the competence-inducing cornAP operon of Bacillus subtilis that also utilizes a peptide for autoinduction (Guangyong et al., *Proc. Natl. Acad. Sci. USA*, 92:12055–12059 (1995); Balaban and Novick, *Proc. Natl. Acad. Sci. USA*, 92:1619–1623 (1995)).

Activation of AgrA also leads to an increased transcription of the δ-hemolysin gene (hld) which is located immediately upstream of the agr operon encoding AgrA (Janzon et al., *Molo. Gen. Genet.* 219:480–485 (1989)) and which is transcribed from the divergent promoter, P3. Transcription from P3 produces a 0.5 kb transcript, RNAIII, which codes for δ-hemolysin. δ-Hemolysin is a small polypeptide of only 26 amino acids (Fitton et al., 1980, *FEBS Lett.* 115:209–212) which is secreted without a signal peptide (Fitton et al., 1980). An insertion in the RNAIII region, distal to the δ-hemolysin coding region inactivates agr global function, but does not interfere with the activity of the two promoters, P2 and P3. Since the signal transduction elements in the P2 operon are not affected, this indicates that a product of the P3 region encodes a critical regulator of the agr response (Novick et al., *EMBO J.* 12:3967–3975 (1993)). (Note that P3 and the hld/RNAIII gene is considered herein to be part of the agr locus.)

However, strains which are defective in agrA or agrC of the P2 operon are agr– and lack both P2 and P3 transcripts. Specifically, since agrA is required for P3 transcription, and since P3 transcription is needed for agr activation of exoprotein synthesis, this indicates that there are at least two sequential regulators. Induction of RNAIII under the control of a β-lactamase promoter in the absence of any other elements of the agr system activates both the positive and negative functions of the agr response, indicating that a P3 product is the actual regulator of the exoproteins. Mutation and deletion analysis indicate that RNAIII itself, rather than a translation product, is the effector. Further, the regulation by RNAIII is primarily at the transcription level, but in some cases also at translation. (Novick et al., *EMBO J.* 12:3967–3975 (1993).)

Figure 1:
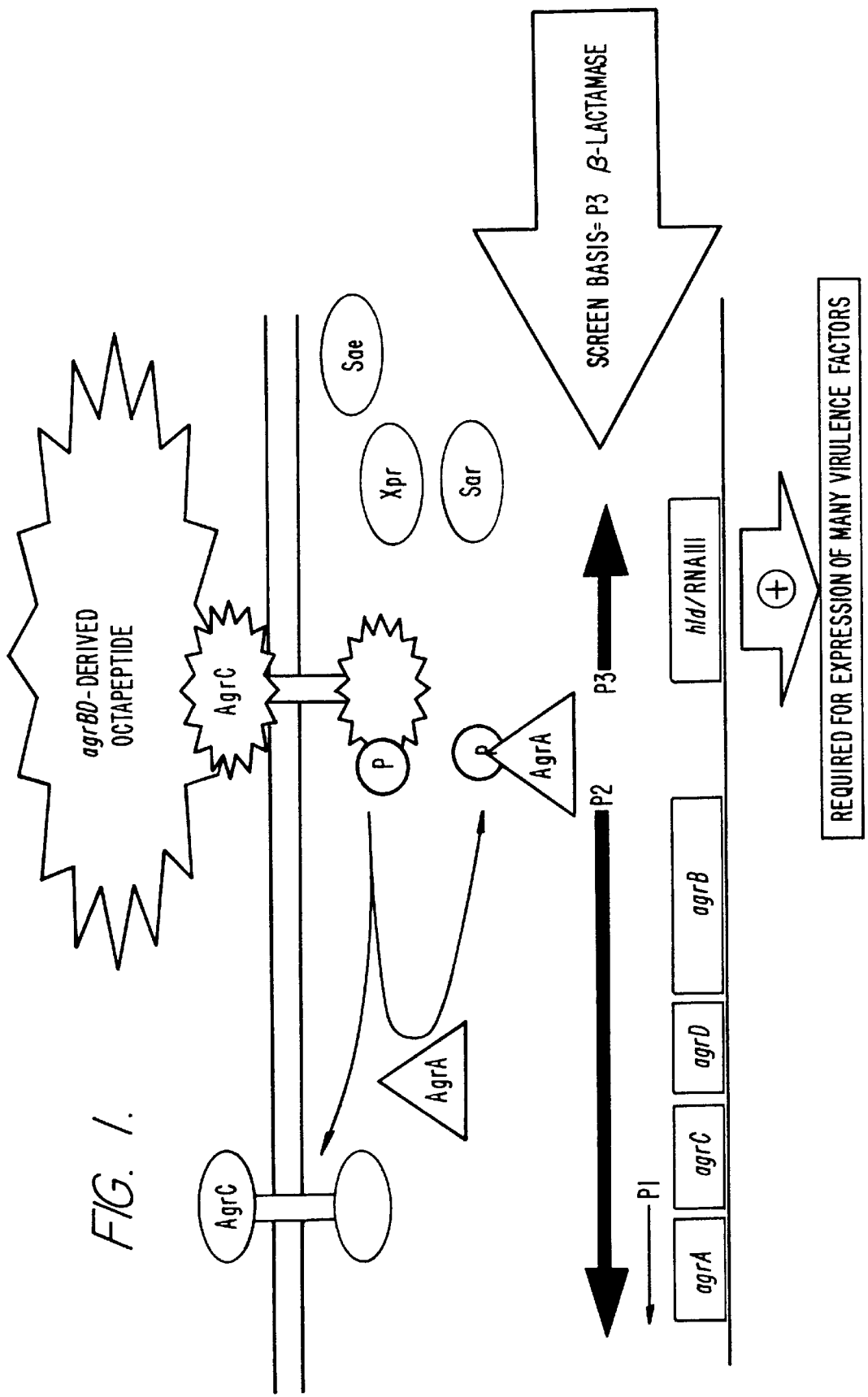
FIG. 1. Schematic representation of the Agr operon and related pathways. The Agr operon is comprised of three promoters driving five genes (agr ABCD, and hld) as well as one regulatory RNA molecule (RNAIII) whose coding sequence overlaps that of hld. AgrC/A are thought to constitute a two-component regulatory system, where AgrC is the putative sensor/kinase and AgrA is the response regulator.

Thus, induction of RNAIII subsequently influences expression of many pathogenesis-related genes, and FIG. 1 summarizes this global regulation (Janzon and Arvidson, *EMBO J.* 9:1391–1399 (1990); Novick et al., *EMBO J.* 12:3967–3975 (1993) Guangyong et al. *Proc. Natl. Acad. Sci. USA.* 92:12055–12059 (1995); Balaban and Novick. *Proc. Natl. Acad. Sci. USA.* 92:1619–1623 (1995); Novick et al., *Mol. Gen. Genet.* 248:446–458 (1995)).

In addition to the agr system, FIG. 1 also identifies other gene products (Xpr, Sar, and Sae) from other global regulatory loci that were shown to interact with, influence, or contribute to the overall regulation of pathogenesis factors, including those shown to be regulated by the agr locus. For example, the regulatory locus xpr, identified by a Tn551 insertional inactivation of a chromosomal site distinct from the agr locus, also reduces the expression of several *S. aureus* exoproteins. These observations suggest that xpr and agr behave as interactive global regulators (Smeltzer et al., 1993, *Infect. Immun.* 61:919–925).

Similarly, other studies have shown that inactivation of the sar locus, also distinct from the agr and xpr loci, results in abnormal exoprotein expression (Cheung & Projan, 1994, *J. Bacteriol.* 176:4168–4172; Cheung et al., 1992, *Proc. Natl. Acad. Sci. USA* 89:6462–6466. Phenotypic and transcriptional studies revealed that the sarA gene is required for the maximal expression of RNAIII and consequently shows an interactive regulation of exoproteins by both the agr and sar loci. Most recently, it was strongly suggested that the sar locus regulates binding to the P2 promoter of the agr locus (Heinrichs et al., 1996, *J. Bacteriol.* 178:418–423). Such interactive regulation between the sar and agr loci should allow the identification of inhibitors of sar by the design of promoter-fusion screens. For example, for such a purpose, the P3 promoter of the promotor-fusion construct disclosed herein can be substituted by the P2 region to evaluate the inhibitory effect of test compounds on sar by measuring the level of expression of the reporter gene under the control of P2.

Another distinct regulatory locus, termed sae, was also identified by an insertional inactivation that produced a mutant defective in the production of several exoproteins (Giraudo et al., 1994, *Can. J. Microbiol.* 40:677–681). However, in this case, the phentotypic characteristics of the mutant were different from the other insertional pleiotropic mutations, agr, sar, and xpr, and it is not known at this time exactly how this locus exerts its global regulation.

Finally, another locus, as yet unnamed, was also shown to have pleiotropic effects on the expression of both exoproteins and cell wall associated proteins. The latter locus is also distinct from agr, xpr, and sar, but remains to be further investigated (Cheung et al., 1995, *J. Bacteriol.* 177:3220–3226).

Previous work by several laboratories has established that mutation of agr reduces virulence in mice. Smeltzer et al., *Infect. Immun.* 61:919–925 (1993) created Tn551 insertions at either the agr or the related xpr locus. No mortality was observed after introduction of high inocula of either of these mutants to the peritoneal cavity of BalbC mice, as compared with 67–100% mortality of control mice injected with parent wild type strains.

In a mouse arthritis model, Abdelnour et al., *Infection and Immunity* 61:3879–3885 (1993) showed higher virulence of parent wild type strains than of agr or hld mutants (also created by Tn551 insertion), as measured by swelling, erythema, synovitis, and erosivity, as well as by histopathology and bacteriology. Interestingly, bacteria were not culturable from joints of mice previously intravenously injected with either agr or hld mutants, as compared to the joints of mice intravenously injected with wild type *Staphylococci*, where 78% produced positive cultures. These experiments were performed 21 days after intravenous injection.

A transcriptional fusion between a regulated promoter of the agr locus (P3) and a reporter gene (β-lactamase) was developed that provides a first-round screen for compounds that prevent Agr-mediated regulation (FIG. 2). (A P3-β-lactamase fusion is described in Novick et al., 1995, *Mol. Gen. Genet.* 248:446–458.) The screen is based on a simple enzyme assay that can be performed on whole cell cultures grown with and without addition of the potential antipathogenic. To be classed as an antipathogenic, the compound should reduce activity of the reporter gene in the Agr+ background at sub-MIC (Minimum Inhibitory Concentration) levels. While the construction of a hybrid DNA including a promoter, P3, from a bacterial global pathogenesis regulator gene of the agr locus, the *S. aureus* RNAIII gene, linked to a reporter gene is described below, it should be recognized that the promoter from any global regulator of pathogens may be used. A reporter gene for use in the hybrid DNA construct can be any gene whose product is readily specifically detected, such as an enzyme which can produce a readily detectable effect. This specifically includes a β-lactamase gene, since a β-lactamase can be readily detected by colorimetric assay or by resistance to the presence of a cleavable β-lactam, like penicillin. However, the reporter could also be a different enzyme detectable by biochemical—assay or a different resistance factor detectible by appropriate antibiotic selection.

This strategy has at least three significant virtues. First, the process can be repeated on virtually any promoter region that is identified as part of a global regulatory cascade, independent of additional (and time consuming) molecular and biochemical analysis of the gene product. Second, the screening system can be standardized for the reporter assay—inhibitors of different genes can be screened by an identical method. Third, such fusion assays can detect any upstream contributor to expression of the global regulatory pathway. Thus, inhibitors of several targets can be simultaneously sought.

As mentioned previously, the centerpiece of the regulation of pathogenesis by Agr is a two-component regulatory system involved in signal transduction. Because these signal transduction components (Novick et al., *Mol. Gen. Genet.* 248:446–458 (1995)), as well as the RNAIII transcript have cross-species homology (Vandenesch et al., *FEMS Lett.* 111:115–122 (1993); Axelsson et al., *Appl. Environ. Microbiol.* 59:2868–2875 (1993)), the effect of test compounds on the expression of virulence factors from other bacterial species is also investigated. Vandenesch et al. showed that sequences related to the *S. aureus* agr are present in *Staphylococcus lugdunensis*, using Southern blot analysis and sequencing data. The −10 and −35 elements of promoters P2 and P3 were highly conserved between the two species, as were several sequences at the putative transcription site for the agr promoters. In addition, the predicted amino acid sequences of *S. lugdunensis* agr-like gene products indicate a substantial degree of sequence similarity between the corresponding gene products for the two species. Such information suggests a high probability that homologs of this global regulator (agr) will also be found in other species. Although possibly weak, the intrinsic growth inhibitory property of test compounds on a large selection of bacterial species is also studied to identify other species whose two-component regulatory systems may be affected by test compounds.

Analogous screens can be produced using known or novel global regulators or two-component regulatory systems. In this regard, it is notable that some of the confirmed hits from the Agr P3-β-lactamase fusion screen were shown to modulate either chemotaxis or sporulation (see below), processes which are also mediated by two-component regulatory systems. Thus, such systems can be assayed microbiologically or biochemically, either secondarily to this or other assays, or novel primary screens can be created in the manner of the Agr Screen. A critical overlap is that these two-component regulatory systems all cause the induction of at least one promoter, so it will invariably be possible to create a reporter-fusion, much as was done with the P3-β-lactamase fusion. Fusion assays are not uncommon, and at least one fusion assay for a two-component regulatory system exists (Roychoudhury et al., PNAS 90:965–969 (1993)). In contrast to the narrow focus on the alginate system in Roychoudhury et al., this invention proposes a broad recognition of the utility of the Agr P3-β-lactamase screen for enriching in molecules that are likely to be active on other orthodox two-component regulatory systems, as opposed to atypical (unorthodox) systems such as the one described for alginate regulation (Parkinson & Kofoid, 1992, Ann. Rev. Genet. 26:71–112). Also, this invention recognizes the broad applicability of this kind of assay for identifying inhibitors of regulatory systems in particular (as opposed to other, more traditional targets such as molecules involved in cell wall or protein synthesis).

Thus, as shown below with some examples, inhibitors of two-component regulatory systems of more distant species controlling other important cellular functions can be found using the P3-β-lactamase fusion screen. In addition, by creating other fusion-specific screens, other regulatory systems can be more specifically exploited.

Examples of other specific regulatory systems, some of which are involved in the pathogenesis of particular organisms, are shown in Table 2.

TABLE 2

Bacterial Two-Component Regulatory Systems

| System | Genes | Signal Transducer and Response Regulator | Organism |
|---|---|---|---|
| Staphylococcal virulence | | AgrC/A (AgrORF2/A)*† | Staphylococcus aureus‡ |
| Staphylococcal virulence | Xpr | ? | S. aureus[1] |
| Staphylococcal virulence | Sar | ? | S. aureus[2] |
| Staphylococcal virulence | Sae | ? | S. aureus[3] |
| Staphylococcal virulence | Agr-sl | ? | Staphylococcus lugdunensis[4] |
| Xanthomonas virulence | Xcc | Xcc2/Xcc1 | Xanthomonas campestris† |
| Xanthomonas virulence | | RpfC | Xanthomonas campestris† |
| Bordetella virulence | | BvgS/BvgA | Bordetella pertussis† |
| Salmonella virulence | Vir | PhoQ/P | Salmonella typhimurium*† |
| Agrobacterium virulence | Vir | VirA or VirA/G | Agrobacterium tumifaciens* |
| Pseudomonal virulence | Lem | LemA/GacA | Pseudomonas syringae, P. viridiflava, P. fluorescens[5] |
| Pseudomonal virulence | Rep | RepA/? | P. viridiflava[6] |
| Klebsiella virulence | | ?/MrkE | Klebsiella pneumoniae† |
| Antibiotic Resistance | Van | VanR/S | Enterococcus faecium† |
| Antibiotic Resistance | Bla | BlaR1/I | S. aureus[7] |
| Antibiotic Resistance | Mec | MecR1/I | S. aureus[6] |
| Antibiotic Stress | RteAgr | RteA | Bacteroides thetaiotaomicron† |
| Heavy Metal Stress | Cut | CutS/R | Streptococcus lividans† |
| Heavy Metal Stress | Pco | ?/PcoR | Escherichia coli† |
| Enzyme secretion | Deg | DegS/U | Bacillus subtilis*† |
| Chemotaxis | Che | CheA/B or CheA/W | E. coli, Enterobacter aerogenes, S. typhimurium*† |
| Nitrogen regulation | Ntr | NRII/I NtrB/A | B. pertussis, E. coli, K. pneumoniae, K. aerogenes, S. typhimurium*† |
| Phosphate regulation | Pho | PhoR/B | E. coli, B. subtilis*† |
| Phosphate regulation | Cre | CreC/B | E. coli† |
| Oxygen regulation | Arc | CpxA/ArcA | E. coli*† |
| Porin expression osmolarity | Omp | EnvZ/OmpR | E. coli, S. typhimurium*† |
| Sporulation | Spo | KinA/B (SpoIIJ) | B. subtilis*† |
| Fruiting body formation Motility | Frz | FrzE | Myxococcus xanthis*† |
| Starvation | Asg | AsgA | M. xanthus† |
| Heptose phosphate uptake | Uhp | UhpB/A | E. coli*† |
| Dicarboxylate transport | Dct | DctB/D | Rhizobium leguminosarum* |
| Tricarboxylate transport | Tct | ?/TctD | S. typhimurium* |
| Phosphoglycerate transport | Pgt | PgtB/A | S. typhimurium* |
| Redox | Nar | NarQ/X/L | E. coli* |
| Competence | Com | ?/ComA | B. subtilis*† |
| Hydrogenase | Hyd | HydH/G | E. coli, S. typhimurium*† |

*As cited in Stock, J. S., A. J. Ninfa, A. M. Stock. 1989. Microbiol. Rev. 53:450–490.
†As cited in Parkinson, J. S., and E. C. Kofoid. 1992. Annu. Rev. Genet. 26:71–112.
‡As cited in Ji, G., R. C. Beavis, and R. P Novick. 1995. Proc. Natl. Acad. Sci. USA. 92:12055–12059.
[1]Smeltzer, M. S., M. E. Hart, and J. J. Iandolo. 1993. Infect. Immun. 61:919–925.
[2]Cheung, A. L., and P. Ying. 1994. J. Bacteriol. 176:580–585.
[3]Giraudo, A. T., C. G. Raspanti, and A. Calzolari. 1994. Can. J. Microbiol. 40:677–681.
[4]Vandenesch, F., S. J. Projan, B. Kreiswirth, J. Etienne, and R. P. Novick. 1993. FEMS Lett. 111:115–122.
[5]Rich, J. J., T. G. Kinscherf, T. Kitten, and D. K. Willis. 1994. J. Bacteriol. 176:7468–7475.
[6]Liao, C. H., D. E. McCallus, and W. F. Fett. 1994. Mol. Plant Microbe Interact. 7:391–400.
[7]Wang, P. Z., S. J. Projan, and R. P. Novick. 1991. Nucl. Acids Res. 19:4000.
[8]Tesch, W., C. Ryffel, A. Strassle, F. H. Kayser, and B. Berger-Bachi. 1991. Antimicrob. Agents Chemother. 34:1703–1706.

C. Description of Primary Screen

1. Fusion Construction.

The Agr assay is designed to identify compounds which inhibit activation of the Agr P3 promoter, and thereby reduce bacterial virulence. The experimental bacterial strain for the protocol is *Staphylococcus aureus* strain 8325-4/pMP25 (strain ISP479C/pMP25, Smeltzer et al, 1993, *Inf. & Imm.* 61:919–925) carrying a recombinant fusion of the Agr P3 promoter to a staphylococcal β-lactamase gene (FIG. 3). It also contains a resistance marker for erythromycin.

2. Rationale and Steps Involved in the Construction of the P3:β-lactamase Fusion.

A staphylococcal reporter gene (the BlaZ β-lactamase) was first placed in a shuttle vector for *E. coli* and *S. aureus*. This was done leaving a restriction site upstream of the reporter for inserting a promoter, in this case, P3 (P3 is synonymous with the hld promoter). In addition, if needed, this construct allows the entire assembly to be removed from the shuttle vector for cloning into an integrative vector for eventual homologous recombination into genomic DNA by cutting with the outermost restriction enzymes flanking the fusion (P3:β-lactamase).

3. Components.

a. The shuttle vector pMIN164 was obtained from the University of Minnesota (Greg Bohach). This vector is a fusion of the *E. coli* pBR328 cloning vector (GenBank Accession #L08858) and *S. aureus* plasmid pE194 (Horinouchi and Weisblum, *J. Bacteriol.* 150:804–814 (1982)), joined at the ClaI site.

b. The β-lactamase gene was from S. aureus strain 76. This strain is a clinical isolate provided by Henry F. Chambers (San Francisco General Hospital) and was shown to produce a β-lactamase by a nitrocefin test (Becton Dickinson Microbiological Systems, Cokeysville, Md.).

c. The hld promoter, P3, was retrieved from pEX07 obtained from S. Arvidson (Karolinska Institutet, Stockholm, Sweden). The pEX07 plasmid contains a 2149 bp BglII-PstI fragment of the agr locus cloned into the cloning vector pSP64 (Janzon and Arvidson, *EMBO J.* 9:1391–1399 (1990)).

4. Method.

a. The endogenous *E. coli* ampicillin-resistance (Ap$^R$) gene from pMIN164 was removed as follows: pMIN164 was cut with restriction enzymes AatII and BsaI, removing an 853 bp fragment which includes most of the Ap$^R$ gene. The ends were filled with T4 DNA polymerase making them blunt before the vector fragment was purified on Nusieve agarose and self-ligated.

b. The β-lactamase gene was obtained by PCR from *S. aureus* strain 76. Primers were chosen from the sequence of the published staphylococcal gene, blaZ (Wang and Novick, *J. Bacteriol.* 169:1763–1766 (1987)). Primers were also designed to contain a BamHI site at the 5' end and a SalI site at the 3' end for cloning into those sites within the tetracycline resistance marker in the pBR328 portion of the shuttle vector.

The primers used are described below. The restriction sites are shown in bold and the nucleotide positions, nt, refer to the sequence of blaZ published by Wang and Novick (*J. Bacteriol.* 169:1763–1766 (1987)).

```
A. Oligo "blaZ-1": 5'primer (SEQ ID NO. 1).
   5'-CGGGATCCATAAAAATTACAACTG-3'   (24-mer)
      BamHI     nt 105 (blaZ)
```

```
-continued
B. Oligo "blaZ-2": 3'primer (SEQ ID NO. 2).
   5'-ACGCGTCGACGAATATTAAAATTCCTTCATTAC-3'
   (33-mer)
      SalI     nt 968 (blaZ)
```

Oligonucleotides were synthesized using the ABI Model DNA Synthesizer. PCR amplification was performed using DNA released from whole *S. aureus* strain 76 cells as the DNA template. Taq Polymerase from Perkins-Elmer was the source of enzyme. The PCR product including restriction sites was 900 bp. The PCR product was digested with BamHI and SalI for cloning into the corresponding sites of pMIN164 having a deleted Ap$^R$ (see step 1 above).

c. The hld gene promoter (P3) was obtained by PCR from pEX07. Primers were also designed to contain BamHI sites at both 5' and 3' ends for joining to the cloned staphylococcal blaZ in the BamHI site of the shuttle vector (see step 2 above).

The primers used are described below. The restriction sites are shown in bold and the nucleotide positions, nt, refer to the sequence of hld published by Janzon et al., *Mol. Gen. Genet.* 219:480–485 (1989).

```
A. Oligo "hld-1": 5'primer (SEQ ID NO. 3).
   5'-CGGGATCCTTTGTATTTAATATTTTAC-3'   (28-mer)
      BamHI     nt 1016 (hld)
```

```
B. Oligo "hld-2": 3'primer (SEQ ID NO. 4).
   5'-CGGGATCCGATCTAGTTATATTAAAAC-3'   (27-mer)
      BamHI     nt 925 (hld)
```

Oligonucleotides were synthesized using the ABI Model DNA Synthesizer. PCR amplification was performed using plasmid pEX07 as the DNA template. Taq Polymerase from Perkin-Elmer was the source of enzyme. The PCR product including restriction sites was 117 bp. The PCR product was digested with BamHI and ligated to the cloned staphylococcal blaZ in the BamHI site of the shuttle vector.

d. The proper configuration of the fusion construct was verified by restriction digests, PCR amplifications and sequencing. Sequencing was performed using the Sequenase protocol (version 2.0, USB, Cleveland, Ohio) and the hld-1 and hld-2 primers. The resulting map of the recombinant plasmid pMP25 is illustrated in FIG. 3.

e. The recombinant plasmid pMP25 isolated from *E. coli* was placed into *S. aureus* by electroporation of strain RN4220, a restriction deficient derivative of strain 8325-4 used as primary recipient for plasmids propagated in *E. coli* (Janzon and Arvidson, *EMBO J.* 9:1391–1399 (1990)). Thereafter, transduction experiments using bacteriophage φ-11 allowed transfer of pMP25 from *S. aureus* RN4220 to both strain 8325-4 (ISP479C) (an Agr+ background) and strain RN6911. Strain RN6911 is an Agr null mutant (Agr-) in which a 3359 bp fragment of the genomic agr locus was replaced with a 3000 bp fragment encoding tetracycline resistance (Nesin et al., *Antimicrob. Agents Chemother.* 34:2273–2276 (1990); Novick et al., *EMBO J.* 12:3967–3975 (1993)). Tests using *S. aureus* strains 8325-4/pMP25 (ISP479C/pMP25) and RN6911/pMP25 were then performed to confirm the proper regulation of β-lactamase (BlaZ) expression under the control of the P3 promoter (see below).

Although copy number and stability of the plasmid did not represent problems in preliminary screening, the fusion construct can also be integrated in the chromosome if such problems occur in specific circumstances. The negative control strain for this assay is S. aureus RN6911/pMP25 (an agr null mutant, Agr-). Neither strain expresses detectable (endogenous) β-lactamase in the absence of plasmid.

Staphylococcal exotoxins are produced in the early stationary phase of growth which mimics in vivo growth. In vitro expression of β-lactamase from the P3:β-lactamase fusion construct showed appropriate temporal regulation (induction in the early stationary phase of growth) as shown in FIG. 4. Also, the Agr dependence of expression of β-lactamase from the P3-β-lactamase fusion was demonstrated by comparing expression in Agr+ and Agr− backgrounds (FIG. 4).

5. Compounds to be Screened

The screening method of the present invention is appropriate and useful for testing compounds from a variety of sources for possible inhibitor activity. The initial screens were performed using a diverse library of compounds, but the method is suitable for a variety of other compounds and compound libraries. Such compound libraries can be combinatorial libraries, natural product libraries, or other small molecule libraries. In addition, compounds from commercial sources can be tested, as well as commercially available analogs of identified inhibitors.

Further, the methods are suitable as part of a medicinal chemistry program to identify derivatives and analogs of screening hits also having activity on global regulators of pathogenesis genes. Typically, such a program is directed to finding compounds having greater activity and/or other improved pharmacologic characteristics (e.g., improved characteristics relating to solubility, toxicity, and stability). Thus, such derivative and analogs can be evaluated or screened for the appropriate activity and other characteristics determined. For example, the methods of screening described herein can be used to determine the activity of such compounds. In particular, the compounds described herein as screening hits, compounds having structures corresponding to the described generic structures, and other derivatives of those compounds can be evaluated or screened, and can themselves provide the bases for further derivatization and screening. As indicated above, some analogs can be obtained from commercial sources; others can be obtained by chemical modification of available compounds or synthesized by methods known to those skilled in the art.

Since many of the compounds in libraries such as combinatorial and natural products libraries, as well as in natural products preparations, are not characterized, the screening methods of this invention provide novel compounds which are active as inhibitors or inducers in the particular screens, in addition to identifying known compounds which are active in the screens. Therefore, this invention includes such novel compounds, as well as the use of both novel and known compounds in pharmaceutical compositions and methods of treating.

EXAMPLE 1

Initial Screen

The Agr screen is performed as follows. Agr+ cells harboring the plasmid with the P3:β-lastamase fusion are diluted from a fresh overnight culture in Trypticase Soy Broth (TSB) to an optical density at 600 nm (O.D. 600 nm) between 0.01 and 0.015. As a positive control, four wells of a 96-well microtiter dish contain these dilute Agr+/P3: β-lactamase cells without added compound. As a negative control for Agr P3 activity, four wells contain Agr− cells harboring the same plasmid, grown and diluted in the same manner as the Agr+ cells. As a negative control for growth, eight wells contain TSB with no inoculum. To test the activity of compounds, 180 μl of the dilute Agr+/P3:β-lactamase inoculum are placed in the remaining wells, which contain 20 μl test compounds at 100 μg/ml (10 μg/ml final) and the plate is placed in a humidified incubator at 35° C. for 6 hours. At this point the O.D.600 for the plate is read, and 20 μl from each well are transferred to a fresh 96-well plate containing 80 μl/well 0.25 mM nitrocefin (a chromogenic cephalosporin) which becomes red upon hydrolysis by β-lactamase enzymes with a maximal absorbency at 490 nm. A compound is considered a hit when β-lactamase activity is significantly inhibited, and growth is not significantly inhibited by that test compound at the same concentration. FIG. 5 shows an example of a screen plate containing a hit (well A4 has no β-lactamase activity although growth was unaffected). For data analysis, the algorithms shown in the brief description of FIG. 5 are used to calculate results. Based on those results the test compounds can be characterized according to biological activity as, for example, a growth inhibitor, a growth retardant, an inactive compound (no effect), an active compound (a potential inhibitor of the Agr system), or an inducer (potential inducer of the Agr system).

D. Secondary Evaluation

Raw hits detected in the primary Agr screen may be β-lactamase inhibitors, weak or selective protein synthesis inhibitors, environmental signal inhibitors, broad signal transduction inhibitors, specific AgrAC inhibitors, or inhibitors acting on regulation steps other than AgrAB, possibly Xpr, Sae and Sar (Smeltzer et al., *Infect. Immun.* 61:919–925 (1993); Cheung and Projan, *J. Bacteriol.* 176:4168–4172 (1994); Giraudo et al., *Can. J. Microbiol.* 40:677–681 (1994); Heinrichs et al. J. Bacteriol. 178:418–423 (1996)) and others (Cheung et al. J. Bacteriol. 177:3220–3226 (1995)). Therefore, the effect of hits on non functional mutants of such genes (xpr, sae, and sar) or of individual components of regulatory operons (ex. either AgrA, B, C, or D in the Agr operon), as well as a battery of secondary tests are appropriate to better characterize screen hits and to elucidate their mode of action. Secondary characterization of hits may be done using the tests outlined below.

EXAMPLE 2

β-Lactamase Inhibition Studies

β-Lactamase inhibition studies are performed with isolated Staphylococcal enzyme purified from *S. aureus* strain 76 and from which the β-lactamase gene was used in the fusion construct. β-lactamase purification was done by the method of Kernodle et al., *Antimicrob. Agents Chemother.* 34:2177–2183 (1990) using a cellulose phosphate cation exchange matrix. The isolated enzyme is pre-incubated with various concentration of test compound for 1 hour at 35° C. (simulating the Agr screen conditions) prior to the addition of the chromogenic substrate nitrocefin to follow β-lactamase activity (O'Callaghan et al., *Antimicrob. Agents Chemother.* 1:283–288 (1972)). Clavulanic acid is used as the inhibitor control. To be carried forward for further characterization and evaluation, a hit should not appreciably inhibit β-lactamase (or other reporter enzyme being used).

EXAMPLE 3

RNAIII and Exotoxins

An Agr inhibitor should alter expression of RNAIII and of the Agr− regulated exotoxins. Expression of hemolysins α, β and δ, and of DNase, enterotoxin B, protease V8 and lipase is normally positively controlled by Agr due to the activation of the P3 promoter of RNAIII. An Agr inhibitor should decrease expression of some or all of these proteins and of the RNAIII transcript and indicator tests can be performed as follow:

RNAIII transcription. RNAIII levels are measured by Northern Blot analysis using a modification of the method of Janzon and Arvidson, *EMBO J.* 9:1391–1399 (1990). Briefly, a 368 bp probe was created by PCR using primers designed to amplify the RNAIII fragment between base pairs 1201 and 1569 of the map obtainable by GenBank accession number. (RNAIII itself is encoded between base pairs ~1050–1570.) The template used for PCR was pEX07 (Janzon and Arvidson, *EMBO J.* 9:1391–1399 (1990)). The probe is labeled with UTP-fluorescein using a commercially available kit. Agr– and Agr+ (with and without inhibitors) are cultured in the presence of a maintenance amount of erythromycin (with putative inhibitors, as appropriate) and RNA extracts are performed at various time points (or at specific O.D. levels). The purified total RNA is run on formaldehyde-agarose gels and transferred overnight to charged nylon. The nylon blot is then hybridized overnight with labeled probe and signal is detected using commercially available anti-fluorescein-HRP conjugated-antibody and chemiluminescent reagents. Film is exposed to the freshly worked up blots and developed using an automated film processor. Alternatively, a chemiluminescence-sensitive screen can be used for exposure, and quantitation can be performed on a molecular imager.

In all RNAIII quantitation experiments, both ethidium bromide staining of the gel prior to transfer and the use of a second probe (a RecA gene probe) were used to verify that essentially equivalent amounts of total RNA were loaded in each lane. The RecA probe was constructed as follows: PCR primers were designed to amplify a 1.1 kb fragment from the RecA gene which sequence was obtainable by GenBank accession number L25893. The genomic DNA template was from *S. aureus* strain 8325-4 and the primers were:

recA 5'-CCCTATGTGATGTTTAGCTC-3' (SEQ ID NO 5) recA 5'-TTAGGAGGTCTCGCTATGGA-3' (SEQ ID NO 6)

The RNAIII probe was labeled with UTP-fluorescein and detection was performed as described above.

The following tests (hemolysins, lipase, DNAase, enterotoxin, and protease) are provided for further characterization of hits. Those hits that are effective inhibitors of the Agr response will lower the level (or perceptible activity) of one or more of these enzymes. Some hits may be general signal transduction inhibitors, with less effect on these specific enzymes, but still of interest; these will be identified through the next set of tests under Example 5.

α, γ, δ, and β-hemolysin activity and expression. α-hemolysin and β-hemolysin activity are measured against rabbit or sheep red blood cells, respectively, by titration assay with 0.5–1% blood cells and/or by spot assay for clearing on blood agar plates (Peng et al., *J. Bacteriol.* 170:4365–4372 (1988)). α, γ, δ, and β-hemolysin expression can also be measured by the methods of Cheung and Ying, *J. Bacteriol.* 176:580–585 (1994) and Janzon and Arvidson, *EMBO J.* 9:1391–1399 (1990), using standard immunoblot techniques. Briefly, a small amount of concentrated extracellular fluid is spotted or electroblotted onto nitrocellulose membrane. The membranes are incubated with specific and appropriate anti-hemolysin antibodies. Detection is via any of several available anti-anti-body-enzyme conjugates and commercially available reagents (ex. Sigma Chemicals, Co.).

Lipase. Lipase production is measured on 1% Tween agar plates by measuring clearing around a predetermined quantity of sample (Cheung and Ying, *J. Bacteriol.* 176:580–585 (1994)). A more specific assay for Tributyrin hydrolysis is performed using the method of Smeltzer et al., *Applied and Env. Microbiol.* 58:2815–2819 (1992). Lipase activity is assayed spectrophotometrically by the decrease in absorbance at 450 nm of suspensions of the triglyceride stabilized with low-melt or standard agarose. It has also been possible to adapt commercially available kits for measuring human lipase for the purpose of measuring bacterial lipase.

DNAse. Culture supernatants are placed in wells in Toluidine Blue DNA (TBD) agar. DNase activity is assessed by the presence of a pink zone around the well (Shortle, *Gene* 22:181–189 (1983); Patel et al., *Infection and Immunity* 55:3103–3110 (1987)).

Enterotoxin B. Enterotoxin B can be detected by using standard immunoblot techniques with specific antibodies commercially available (ex. Sigma Chemicals, Co.).

Protease. Staphylococcal protease V8 activity can be detected by using the commercially available chromogenic substrate carbobenzoxy-L-phenylalanyl-L-leucyl-L-A glutamic acid-4-nitroanilide (Boehringer Mannheim, Corp.).

EXAMPLE 4

Protein A and Coagulase

Expression of protein A and of coagulase is normally negatively controlled by Agr, and an Agr inhibitor should increase expression of these proteins. Indicator tests are performed as follows:

Protein A. Protein A expression is assayed by immunoblots of SDS-Page separated total cell proteins (Patel et al., *Infection and Immunity* 55:3103–3110 (1987)).

Coagulase activitty. Culture supernatants are tested for coagulase activity by incubation (37° C., 18 hrs.) with neat rabbit plasma (Patel et al., *Infection and Immunity* 55:3103–3110 (1987)).

EXAMPLE 5

Signal Transduction Systems and Secretion

Compounds acting as general signal transduction inhibitors are of special interest, as such inhibitors may be novel antimicrobial agents. There are several well-characterized or putative bacterial two-component signal transduction systems that can be targeted (see Table 2). Certain of these can easily be used to test the compounds for general signal transduction inhibition. These include but are not limited to: alkaline phosphatase induction, sporulation (*Bacillus subtilis*), and chemotaxis (*B. subtilis, Escherichia coli*, and *Salmonella typhimurium*). In addition, many resistance mechanisms are signal transduction mediated, for example vancomycin resistance, β-lactamase resistance, and methicillin resistance. Finally, signal transduction inhibitors can be distinguished from inhibitors of basic secretion. Agr hits that are not secretion inhibitors but which inhibit one or more of the following signal transduction pathways will be carried forward as general signal transduction hits.

Alkaline Phosphatase induction: Phosphate utilization has been extensively characterized in *E. coli*, and is now well-studied in *B. subtilis* as well. In both species, there is a level of regulation that occurs via a two-component regulatory system; phoR/phoB in *E. coli* (Nakata et al., Genetic and biochemical analysis of the phosphate specific transport system in *Escherichia coli*, pp. 150–155, In A. Torriani-Gorini et al. ed., Phosphate metabolism and cellular regulation in microorganisms, American Society for Microbiology, Washington, D.C. (1987); Wanner, Phosphate regulation of gene expression in *Escherichia coli*, pp. 1326–1333, In F. C. Neidhardt et al. eds., *Escherichia coli* and *Salmonella typhimurium*: cellular and molecular biology, American Society for Microbiology, Washington, D.C. (1987)) and phoR/phoP in *B. subtilis* (Seki et al., *J. Bacteriol.* 169:2913–2916 (1987); Hulett et al., *J. Bacteriol.* 176:1348–1358 (1994)). In *S. aureus*, the phosphatase that is active at pH 8 has been shown to be constitutive in some species and repressed by phosphates in others (Soro et al., *J. Clin. Microbiol.* 228:2707–2710 (1990)), indicating the possible presence of a two-component regulatory system. Alkaline phosphatase is induced in all three organisms after growth in phosphate-limiting media, and can be easily and sensitively assayed using whole cells, supernatants, or various cell fractions. The sample is combined with a calorimetric substrate, p-nitrophenyl phosphate, in a suitable buffer (100 mM Tris, pH 8 with 0.5 mM $MgCl_2$). If alkaline phosphatase is present, the colorless p-nitrophenyl phosphate is cleaved and releases yellow p-nitroaniline. Therefore, enzyme activity can be monitored by the increase in yellow color using a spectrophotometer at 405–410 nm. If a compound interferes with the signal transduction pathway for phosphatase regulation, then growth of the organism in low phosphate medium in the presence of the compound will yield one of two results: it will lower the output of phosphatase per cell as compared to the cultures grown in the absence of compound in low phosphate medium; or, if the phosphate recovery system is sufficiently disabled, it will cause a large decrease in cell growth as compared both to growth in the absence of compound and in low phosphate medium, or in the presence of compound in high phosphate medium.

Sporulation: Sporulation is a well-characterized event in many organisms, including *Bacillus subtilis* (spoIIJ/spo0A or spoIIJ/spo0F, Losick et al., *Annu. Rev. Genet.* 20:625–669 (1986); Smith, The initiation of sporulation, pp. 185–210, In I. Smith et al. eds., Regulation of procaryotic development, American Society for Microbiology, Washington, D.C. (1989)). It can be induced in various media (Leighton and Doi, *J. Biol. Chem.* 246:3189–3195 (1971); Piggot and Curtis, *J. Bacteriol.* 169:1260–1266 (1987)), and can be easily assayed (Nicholson and Setlow, Sporulation, germination, and outgrowth, pp. 391–429, In C. R. Harwood and S. M. Cutting eds., Molecular biological methods for Bacillus, John Wiley and Sons, Ltd., Chichester, West Sussex, England (1990)). Briefly, by heating the cells to 80–85° C. for 15–20 min, undifferentiated cells are killed while spores survive. Therefore, by determining the difference in viable cell count of control cultures versus heat treated cultures, it is possible to calculate the percent sporulation for a given culture or condition. Compounds that inhibit the signal transduction system responsible for the induction of sporulation will lower the viable cell count of the heat treated culture.

Chemotaxis: Motility has been studied in a variety of bacteria. The molecular mechanisms of motility have been best characterized in *E. coli* and *S. typhimurium* but analogs of the molecular components have been detected in both Gram-negative and Gram-positive organisms (Morgan et al., *J. Bacteriol.* 175:133–140 (1993)). A two-component regulatory system composed of either cheA/cheY or cheA/cheB (Stewart and Dahlquist, *Chem. Rev.* 87:997–1025 (1987); MacNab, *Motility and Chemotaxis*, pp. 732–759, In F. C. Neidhardt, et al., ed., *Escherichia coli* and *Salmonella typhimurium*: cellular and molecular biology, American Society for Microbiology, Washington, D.C. (1987)), is central to the ability of these organisms to detect and respond appropriately to chemical substances. Such response can be detected on minimal swarm agar plates containing a chemoattractant (sugars or amino acids) (J. S. Parkinson, *J. Bacteriol.* 126:758–770 (1976)), or a capillary assay system, in which chemoattractant is placed in a capillary tube and immersed in a liquid bacterial culture. Bacteria capable of chemotaxis will swim into the capillary and can be detected by performing viable cell counts (Adler, *J. Gen. Microbiol.* 74:77–91 (1973)). Bacteria are to be tested with capillaries or swarms containing a known chemoattractant, with chemoattractant and test compound in the assay medium, and with no chemoattractant but with test compound in the assay medium to determine the extent of suppression of chemotaxis caused by a given test compound. Inhibitors of the signal transduction components involved in chemotaxis should modulate the ability of the bacteria to swim into the capillary tube, thereby changing the viable cell count, or alter the diameter of bacterial swarms.

Induction of antibiotic resistance. Vancomycin resistance in Enterococci is a complex process that is initiated through a signal transduction pair, vanR/vanS (Arthur et al., *J. Bacteriol.* 174:2528–2591 (1992); Wright et al., *Biochemistry* 32:5057–5063 (1993)). Using inducible vancomycin resistant strains of *Enterococcus faecium*, it is possible to detect inhibitors of the initial step in resistance (induction of resistant genes in the presence of vancomycin) by performing synergy studies with vancomycin. An inhibitor of the signal transduction pair should cause such an organism to become more sensitive to vancomycin, reducing the MIC to vancomycin.

β-lactamase induction. Studies on the induction and secretion of β-lactamase as well as synergy studies with β-lactams in *S. aureus* strains carrying the plasmid p1258 will provide answers to several questions. Expression of the blaZ β-lactamase is normally induced by β-lactam molecules through the blaR1/blaI signal transduction pathway (Wang et al., *Nucl. Acids Res.* 19:4000 (1991); Bennett and Chopra, *Antimicrob. Agents Chemother.* 37:153–158 (1993)), and inhibitors of this non-traditional signal transduction pathway should be detected by induction studies with cells pre-exposed to the test compounds. If inhibitors are found, it should also be possible to show that they are synergistic with traditional β-lactam drugs. In addition, it has recently been shown that the blaR1/blaI system may engage in crosstalk with the signal transduction pair involved in staphylococcal methicillin resistance, mecR1/mecI, which regulate the expression of the major methicillin resistance factor, PBP2a (Tesch et al., *Antimicrob. Agents Chemother.* 34:1703–1706 (1990);

Hiramatsu et al., *FEBS Lett.* 298:133–136 (1992)). Therefore, synergy studies on methicillin-resistant *S. aureus* (MRSA) will also be of use in demonstrating general signal transduction inhibition.

Compounds that show inhibitory activity in these or other microbial signal transduction systems will be of interest and will be carried forward for further study, including in vivo study.

Secretion may be evaluated with the same system using, this time, cells already induced for β-lactamase production prior to exposition to test compounds. Those compounds that create defects in secretion of β-lactamase will be considered to be in a separate category from signal transduction inhibitors, unless the cause of the secretion defect is eventually shown to originate in signal transduction inhibition.

EXAMPLE 6

Membrane Interactions

To study the possible non-specific effect of the Agr screen hits on systems that involve membrane protein function in *S. aureus*, the lactose metabolism pathway may be used (Rosey et al., *J. Bacteriol.* 173:5992–5998 (1991); Simoni et al., *J. Biol. Chem.* 248:932–940 (1973)). Growth of *S. aureus* on lactose leads to the induction of the lactose phosphoenolpyruvate phosphotransferase system and the effect of test compounds (hits) on lactose utilization may be evaluated by monitoring growth in a defined medium.

Also, cadmium resistance in *S. aureus* carrying plasmid p1258 is due to a specific active efflux pump system (Silver and Walderhaug, *Microb. Rev.* 56:195–228 (1992)) and the effect of test compounds on cadmium resistance may be investigated to provide information on their effects on membrane protein functions.

Finally, fluorescent hydrophobic probes may also be used to study direct effects of test compounds on membrane integrity.

EXAMPLE 7

Protein Synthesis

Additional information on hits may be obtained by studying the effects of test compounds on protein synthesis using a traditional assay system.

E. Pharmacology and in vitro Testing.

In addition to secondary assays for determination of the mode of action of the primary hits, other in vitro tests are also appropriate for collecting pharmacological data, such as the following:

EXAMPLE 8

Synergism/Antagonism Studies

Standard checkerboard assays are designed to examine drug interactions in vitro. Generally, a two dimensional matrix of two drugs (or test compound versus known drug) is created such that both drugs vary in concentration. The effect of the various combinations is measured by examining the MIC or MBC for the particular set of concentrations and comparing this to the summed effects of the drugs alone using a relation known as the fractional inhibitory concentration index (FIC index). In this screen, the effects of the drug combinations on the β-lactamase activity under the control of the P3 promoter as well as the antibacterial activity of the known drugs and combinations can be monitored. The FIC index will provide the type of drug interactions: additive, synergistic, or antagonistic (Eliopoulos and Moellering, Antimicrobial Combinations, p. 432–492, In Lorian (Ed.), *Antibiotics in Laboratory Medicine*, 3rd ed., The Williams & Wilkins Co., Baltimore (1991)). A nonstandard index based on the FIC index can be developed using the concentration at which a preselected percent inhibition of β-lactamase activity is observed in place of the MIC, and this index will provide a measure of whether the drugs interact with respect to antipathogenesis activity.

EXAMPLE 9

Spectrum of Activity

The effect of test compounds on the expression of virulence factors from several clinical strains of *S. aureus* may be determined. Initial tests that can be performed on various strains grown in the presence of the test compounds include detection of RNAIII, α-hemolysin, DNase and lipase by agar plate assays as well as a coagulase slide test and immunodetection tests for enterotoxin B and protein A.

EXAMPLE 10

Extended Spectrum of Activity

The effect of test compounds on growth of other organisms may also be assessed using standard MIC testing (microdilution or agar dilution).

EXAMPLE 11

Toxicity

Potential toxicity to eukaryotes is preferably tested in vitro using yeast or mammalian cell cultures and colorimetric tests for prediction of acute toxicity in vivo (Garle et al., *Toxic. in Vitro*, 8:1303–1312 (1994)).

EXAMPLE 12

Serum Effects

The effect of serum on the observed activity of the test compounds is also evaluated (i.e., serum protein binding, serum inactivation of compounds, etc.).

EXAMPLE 13

Analog Testing

Structural analogs of hits are purchased, synthesized, or otherwise obtained from various sources for testing in the Agr screen as an initial structure activity relationship study.

Such synthesis of analogs, or chemical modification of identified screening hits, generally utilize synthetic and chemical modification methods known to those skilled in the art. In certain circumstances, analogs which are synthesized or created by chemical modification from identified screening hits are novel compounds. Such novel compounds which are active in the screening methods of this invention and/or are active on global pathogenesis regulators are within the scope of this invention.

F. Pharmacology and in vivo Testing.

EXAMPLE 14

In vivo Evaluation of Microbial Virulence and Pathogenicity

Confirmation of specificity of activity and other in vitro evaluations is done before in vivo testing is begun. The criteria for evaluation in vivo includes ability of the bacteria to replicate, the ability to produce specific exoproducts involved in virulence of the organism, and the ability to cause symptoms of disease in the animals. In vivo evaluation follow protocols developed in light of the specific activities of the Agr inhibitors. Efficacy of the inhibitors alone and in combination with antibiotics is studied. The ability to down-regulate specific staphylococcal virulence factors is examined.

Six exemplary animal infection models appropriate for use to evaluate the effects of Agr screen hits are described below. The animal models are selected for efficiency, reproducibility and cost containment. Rodents, especially mice and rats, are generally the preferred species as experimentalists have the greatest experience with these species. Manipulations are more convenient and the amounts of materials which are required are relatively small due to the size of the rodents.

The mouse soft tissue infection model is a sensitive and effective method for measurement of bacterial proliferation. In this model, anesthetized mice are infected with the bacteria in the muscle of the hind thigh. The mice can be either chemically immune compromised (e.g. cyclophosphamide treated) or immunocompetent. The dose of microbe necessary to cause an infection is variable and depends on the individual microbe, but commonly is on the order of 10 exponent 6 colony forming units per injection for bacteria. A variety of mouse strains are useful in this model although Swiss Webster and DBA2 lines are most commonly used. Once infected the animals are conscious and show no overt ill effects of the infections for approximately 12–24 hours, depending on the strain used. After that time virulent strains cause swelling of the thigh muscle, and the animals can become bacteremic within approximately 24 hours. This model most effectively measures proliferation of the microbe, and this proliferation is measured by sacrifice of the infected animal and counting viable cells from homogenized thighs.

The diffusion chamber model is useful as second model for assessing the virulence of microbes (Dargis et al., *Infect. Immun.* 60:4024–4031 (1992); Malouin et al, *Infect. Immun.* 58:1247–1253 (1990)). In this model, rodents have a diffusion chamber surgically placed subcutaneously or in the peritoneal cavity. The chamber can consist of a polypropylene cylinder with semipermeable membranes covering the chamber ends. Diffusion of interstitial or peritoneal fluid into and out of the chamber provides nutrients for the microbes. The progression of the "infection" can be followed by examining growth, the exoproduct production or RNA messages. The time course experiments are done sampling multiple chambers. Bacterial toxins and other exoproducts are produced and are measurable from cells grown in these chambers. Bacteria can persist at high concentrations for up to at least several days in this model.

The endocarditis model is an important animal model effective in assessing pathogenicity and virulence for bacteria. Either a rat endocarditis model or a rabbit endocarditis model can be used to assess colonization, virulence and proliferation of bacteria in animals treated with test compounds having antipathogenic activities.

The osteomyelitis model is a fourth model useful in the evaluation of pathogenesis. Rabbits are used for these experiments. Anesthetized animals have a small segment of the tibia removed and microorganisms are microinjected into the wound. The excised bone segment is replace and the progression of the disease is monitored. Clinical signs, particularly inflammation and swelling are monitored. Termination of the experiment allows histologic and pathologic examination of the infection site to complement the assessment procedure.

The murine septic arthritis model is a fifth model relevant to the study of microbial pathogenesis. In this model mice are infected intravenously and pathogenic organisms are found to cause inflammation in distal limb joints. Monitoring of the inflammation and comparison of inflammation vs. inocula allows assessment of the virulence of bacteria in animals treated with test compounds having antipathogenic activities.

Bacterial peritonitis offers rapid and predictive data on the virulence of strains. Peritonitis in rodents, preferably mice, can provide essential data on the importance of targets. The end point may be lethality or clinical signs can be monitored. Variation in infection dose in comparison to outcome allows evaluation of the virulence of bacteria in animals treated with test compounds having antipathogenic activities.

G. Screen Results.

Table 3 shows the characteristics of several of the hits identified in the screen, and how they were classified as active compounds (putative Agr inhibitors or inducers) by the screen algorithms described herein (see Brief Description of FIG. 5). The compounds are defined as "active" (inhibitor) or "inducer" in the Agr P3-β-lactamase fusion assay. The percent growth compared to untreated Agr+ cells and the % inhibition of β-lactamase (after correction for cell density) is shown for various concentrations of several hits.

Using such screen design and calculations, traditional drugs such as ciprofloxacin or vancomycin do not behave as hits using these algorithms.

TABLE 3

Confirmed Hits from the Agr P3-β-lactamase Fusion Assay with Results derived from the Screen Algorithm

| Compound | Growth (%) | β-Lactamase inhibition (%) | Status from algorithm |
| --- | --- | --- | --- |
| 1 | 105 | 75 | Active |
| 2 | 122 | 84 | Active |
| 3 | 70 | 83 | GR and Active |
| 4 | 113 | 86 | Active |
| 5 | 84 | −36 | Inducer |
| 6 | 72 | −111 | GR and Inducer |
| 7 | 103 | 87 | Active |
| 8 | 101 | 84 | Active |
| 9 | 91 | 86 | Active |
| 10 | 107 | 84 | Active |
| 11 | 104 | 77 | Active |
| 12 | 124 | 76 | Active |
| 13 | 111 | 75 | Active |
| 14 | 94 | 77 | Active |
| 15 | 101 | 76 | Active |
| 16 | 106 | 78 | Active |
| 17 | 87 | 83 | Active |
| 18 | 89 | 75 | Active |

FIGS. 6–8 provide the chemical structures of 18 hit compounds found in the screen. The structures of the specific hits shown in FIGS. 6–8 are also represented by generic structures (FIGS. 9–12), which correspod to the broader classes of compounds likely to have similar activity.

Titration assays were used to characterize hits and demonstrated a dose response of β-lactamase expression with rising test compound concentration in several cases (FIG. 13), indicating a specificity in the mode of action of such hits.

Subsequent characterization studies on many of the hits has also shown that the these hits were not specific inhibitors of the Staphylococcal β-lactamase enzyme used as the reporter molecule in the screen (data not shown).

In addition to the active hits characterized as putative Agr inhibitors, two molecules were identified (Compounds 5 and 6, Table 3) that enhance the production of β-lactamase, indicating possible induction of the P3 promoter. These molecules will be referred to as "inducers". Overall, 15 of the 16 hits tested caused a quantitative decrease in production of RNAIII, as assayed by Northern Blot, whereas an inducer (Compound 6) allowed overexpression of RNAIII (See examples and FIGS. 14 and 15). In addition, several compounds lowered the signal from u-hemolysin (an Agr positively-controlled exotoxin) in both a plate assay and immunoblot (FIGS. 16 and 17), and lowered signal from staphylococcal enterotoxin B (SEB) in immunoblot analysis (FIG. 17). Accordingly, some putative Agr inhibitors were thus found to increase the level of expression of protein A which is an Agr negatively-controlled surface protein (FIG. 18). In the case of RNAIII, both ethidium bromide staining of the gel prior to transfer and the use of a second probe (for RecA) establish that essentially equivalent amounts of RNA were loaded in each lane; quantitation of recA signal is used for normalization of small differences in load. Glycerol Monolaureate (GML) is a surfactant and putative signal transduction inhibitor that is known to lower the production of several toxins in an Agr independent manner (Schlievert et al., *Antimicrob. Agents Chemother*. 36:626–631 (1992); Projan et al., *J. Bacteriol*. 176:4204–4209 (1994)). In FIGS. 14 and 15, the effect of GML and the inducer are shown for comparison. Furthermore, GML, which showed no effect on RNAIII, did not qualify as a hit in the screen.

One screen hit (compound 18) showed synergy with methicillin against a methicillin resistant and PBP2a producing strain of *S. aureus* (FIG. 19). In addition, a subset of Agr hits that affect chemotaxis or sporulation has been identified. In the case of chemotaxis, one particular hit (compound 11) which is not a chemi-attractant or -repellant itself, deregulated chemotaxis and enhanced swarm diameters of *S. typhimurium* on ribose-containing swarm agar plates. The sporulation hits (compounds 3 and 14) lowered the percent sporulation generated by *B. subtitlis* strain 168 by more than 50% compared to untreated controls.

Table 4 summarizes secondary tests performed with the compounds identified as active compounds (putative Agr inhibitors), or as inducer (compound 6, data for compound 5 not shown) in the P3-β-lactamase fusion screen. As discussed above, hits were characterized by various secondary assays to demonstrate effects of compounds on the global regulator Agr (RNAIII, alpha-hemolysin, lipase, V8 protease, and protein A expression), and on other two-component regulatory systems (sporulation, chemotaxis and specific drug synergy tests).

Finally, as an example, FIG. 20 confirms that the effect of hits observed in secondary tests are also applicable to clinical strains of *S. aureus*. RNAIII expression in several clinical strains of *S. aureus* was shown to be greatly reduced in the presence of compound 10.

TABLE 4

Properties of some confirmed agr screen hits in various tests involving the global regulator or other two component regulatory systems

| Hit | RNAIII | Alpha-Hemolysin | Lipase | V8 Protease | Protein A | Sporulation | Chemotaxis | Drug Synergy |
|---|---|---|---|---|---|---|---|---|
| 1 | + | ++ | ++ | N | N | N | N | nd |
| 2 | ++ | ++ | ++ | + | [++] | N | N | nd |
| 3 | + | ++ | + | + | [++] | ++ | N | N |
| 4 | N | ++ | + | + | nd | N | N | N |
| 6 | [++] | [++] | N | [++] | [+] | N | N | N |
| 7 | ++ | ++ | N | N | nd | N | N | N |
| 8 | ++ | N | N | + | nd | N | N | N |
| 9 | + | ++ | + | + | nd | N | N | N |
| 10 | ++ | ++ | + | + | nd | N | N | nd |
| 11 | ++ | ++ | + | + | nd | N | [++] | nd |
| 12 | ++ | ++ | + | N | nd | N | nd | N |
| 13 | ++ | ++ | ++ | + | nd | N | N | N |
| 14 | ++ | ++ | ++ | + | nd | ++ | N | nd |
| 15 | + | ++ | ++ | + | nd | N | N | N |
| 16 | ++ | ++ | ++ | N | nd | N | N | N |
| 17 | ++ | ++ | + | N | nd | N | N | N |
| 18 | ++ | ++ | ++ | + | nd | N | N | ++ |

++: Compounds that reduce expression of RNAIII, alpha-hemolysin, lipase, or V8 protease by more than 50% compared to expression levels observed in untreated wild type controls (Agr+ *S. aureus* cells). Also indicated by an identical symbol are compounds that decrease *B. subtilis* sporulation by more than 50% and compounds that act synergistically in combination with drugs such as methicillin against *S. aureus*.
+: Compounds that reduce expression of RNAIII, alpha-hemolysin, lipase, or V8 protease by 25% to 50% compared to production levels observed in untreated wild type controls (Agr+ *S. aureus* cells).
[++]: Compounds that increase expression of RNAIII, alpha-hemolysin, lipase, or V8 protease by more than 50% compared to expression levels observed in untreated wild type controls (Agr+ *S. aureus* cells). Also indicated by an identical symbol are compounds that increase *S. aureus* protein A expression to at least 50% of the level of expression observed in Agr– mutant cells and compounds that increase *Salmonella typhimurium* chemotaxis compared to controls.
N: Compounds lacking significant effect in the indicated tests.
nd: Not determined.

H. Inducers—Identification and Use

As shown in Tables 3 and 4 above, two of the compounds (Compounds 5 and 6) identified using the P3-β-lactamase screen showed inducer rather than inhibitor activity, as defined by the screen algorithim (see brief description for FIG. 5). As shown in Table 4, Compound 6 increased the level of activity of certain other cellular activities. Additional inducers can be identified by testing of analogs of identified inducers, as well as by additional screening of compounds. Inducer compounds, in addition to the inhibitor compounds, are useful, and are also within the scope of this invention.

In certain regulatory systems, an inducer of a particular signal inhibits a particular pathogenesis-related response(s). In such cases, such an inducer of a regulator which decreases a pathogenic response may be used in a manner similar to an inhibitor of a regulator which decreases a pathogenic response. Thus, such inducers can be utilized in therapeutic compositions and methods of treating.

In addition, inducer compounds can be used as evaluation controls in comparison with inhibitor compounds, and are, therefore, useful test reagents in the methods of this invention.

Further, as described above, in the agr system (as well as in other regulatory systems), a peptide or protein factor acts as a natural inducer of a particular step or steps in a pathogenic response(s) (see Guangyong et al, 1995, *Proc. Natl. Acad. Sci. USA* 92:12055–12059; Balaban & Novick, 1995, *Proc. Natl. Acad. Sci. USA* 92:1619–1623). Balaban & Novick indicated that sera containing antibodies against the octapeptide inducer block activation of the agr response. Therefore, antibodies against small molecule inducers which mimic the binding of a natural inducer can also bind to the natural inducer and block a pathogenic response such as the Agr response. The generation of such antibodies by a small molecule inducer may, in fact, be more efficient than the generation of antibodies by a peptide or protein inducer since it would be expected that such peptides would be rapidly degraded. Therefore, inactive analogs of inducers that would still bind to, or interact with microbial response regulators, and that would compete with the microbe's natural inducers, can be used to generate an immune response in the host and/or to competitively abolish stimulating effects by the natural inducers. Either of these processes would interfere with the development of and/or effects of a particular microbial infection.

As indicated above, two inducer compounds (Compounds 5 and 6) were identified. Therefore, in particular embodiments, this invention includes those compounds and related active compounds described by the general structure, Structure 3, as shown below:

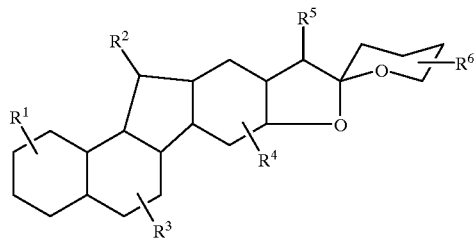

and the corresponding narrower general structure, Structure 3A, below:

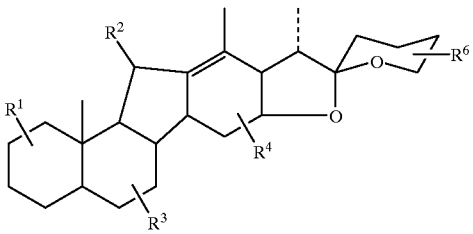

For the compounds described by these structures, $R^1$–$R^6$ may be the same or different, and are selected from the group consisting of H, optionally-substituted $C_1$–$C_4$ alkyl, $C_1$–$C_4$ alkenyl, $C_1$–$C_4$ alkoxy, hydroxy, and amino. The rings shown in the general structures may be saturated or unsaturated. As was described for the identified inhibitor compounds, compounds described by these general structures, related to the identified inducers, can be obtained by a variety of methods, including obtaining analogs from commercial sources, by synthesizing particular analogs, by chemical modification of the known inducers or of available analogs of such inducers, or by additional screening of compounds in appropriate libraries.

I. In vivo Evaluation of Agr Null Mutant.

Using a mucin-enhanced murine peritonitis model with Balb/c mice, reduced virulence of an agr null mutant was also demonstrated. Experiments were performed as follows:

Male Balb/c mice weighing 22–25 g were obtained from Charles Rivers Labs, Hollister, Calif. Mice were housed 10 per cage and given free access to food and water.

*Staphylococcus aureus* strains ISP479C (Agr+) and ISP 546 (Agr–) (Smeltzer et al., 1993, *Inf. & Imm.* 61:919–925) were grown overnight in Tryptic Soy (TSB) broth. The following morning, they were subcultured to fresh TSB and incubated for 4–5 h. Cells were washed twice with PBS and adjusted to the desired concentration by correlation of absorbency at O.D. 600 nm with predetermined plate counts.

Mice were challenged by the intraperitoneal route with 0.5 mL of bacterial suspension in 7% hog-gastric mucin. Animals were observed for 72 h. Table 5 outlines results of such in vivo studies. These data show the difference in virulence of Agr+ and Agr– *S. aureus*, and hence what may be possible to achieve with a compound that inhibits the Agr response.

TABLE 5

In Vivo Effects of Agr+ & Agr– *Staphyloccus aureus* Strains in Mice

|  | Strain ISP479C (Agr+) | Strain ISP547 (Agr–)* |
|---|---|---|
| $LD_{50}$ (cfu): | $2.3 \times 10^7$ | $4.3 \times 10^9$ |
| Challenge dose of $10^8$ cfu: | All mice died | All mice lived |

*Note: A challenge dose of $10^{10}$ cfu was treatable with vancomycin (3.15 mg/kg).

J. Pharmaceutical Applications

The compositions containing inhibitors of global regulators of pathogenesis genes can be administered for prophylactic and/or therapeutic treatments. In therapeutic applications, the compositions are administered to a patient already suffering from an infection from bacteria (similarly for infections by other microbes), in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to, or otherwise at risk of, a particular infection. Such an amount is defined to be a "prophylactically effective amount or dose." In this use, the precise amounts again depend on the patient's state of health, weight, and the like. However, generally, a suitable effective dose will be in the range of 0.1 to 10000 milligrams (mg) per recipient per day, preferably in the range of 10–5000 mg per day. The desired dosage is preferably presented in one, two, three, four, or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 25 mg/kg of patient body weight, between about one to four times per day.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In preferred embodiments of the pharmaceutical compositions, and treatment methods, the inhibitor has a structure as shown by one of the general structures, Structures 1–2 and 4–14, including Structures 1A, 2A, 2B, 4A, 5A, 6A, 7A, 8A, 9A, 10A, 11A, 12A, 13A, and 14A. These general structures correspond to the active inhibitor screening hits as shown in the description of FIGS. 9–12.

In the case of compounds having Structure 1 or 1A, the core structure having two fused 6-member rings and a hydroxy substituent is termed the hydronaphthalene system; the rings of this system may contain from zero to five double bonds. $R^1$, $R^2$, and $R^3$ may be the same or different, and are selected from the group consisting of H, optionally-substituted $C_1$–$C_4$ alkyl, $C_1$–$C_4$ alkenyl, $C_1$–$C_4$ alkoxy, hydroxy, or amino. $R^4$ is an optionally-branched, saturated or unsaturated hydrocarbon chain containing up to ten carbon atoms. If unsaturated, the chain contains from one to four double bonds.

For compounds having Structure 2, 2A, or 2B, $R^1$, $R^2$, and $R^3$ may be the same or different, and are selected from the group consisting of H, optionally-substituted $C_1$–$C_4$ alkyl, $C_1$–$C_4$ alkenyl, $C_1$–$C_4$ alkoxy, hydroxy, or amino. $R^4$ is selected from the group consisting of H, $C_1$–$C_4$ alkyl, $C_1$–$C_4$ alkenyl, $C_1$–$C_4$ alkoxy, or halogen. The rings may contain single or double bonds.

For compounds having Structure 4 or 4A, $R^1$ is selected from the group consisting of H, $C_1$–$C_4$ alkoxy, aryloxy, araalkoxy, $C_1$–$C_4$ alkyl, and aryl. $R^2$ and $R^3$ may be the same or different, and are selected from the group consisting of H, optionally-substituted, optionally-branched $C_1$–$C_4$ alkyl, $C_1$–$C_4$ alkenyl, aryl, or araalkyl. In specific embodiments, $R^2$ and $R^3$, in combination with the groups to which they are attached form known natural and unnatural amino acids. In other embodiments, $R^2$ and $R^3$ do not form natural or unnatural amino acids.

For compounds having Structures 5 or 5A, $R^1$, $R^2$, and $R^3$ may be the same or different, and are selected from the group consisting of H, $C_1$–$C^4$ alkyl, $C_1$–$C_4$ alkenyl, $C_1$–$C_4$ alkoxy, amino, hydroxy, trifluoromethyl, and halogen. $R^4$ is selected from the group consisting of H and $C_1$–$C_4$ alkyl.

For compounds having Structure 6 or 6A, $R^1$ and $R^2$ may be the same or different, and are selected from the group consisting of H, $C_1$–$C_4$ alkyl, $C_1$–$C_4$ alkenyl, $C_1$–$C_4$ alkoxy, amino, hydroxy, trifluoromethyl, and halogen. $R^3$ is selected from the group consisting of H, optionally-substituted $C_1$–$C_4$ alkyl, $C_1$–$C_4$ alkenyl, $C_1$–$C_4$ alkoxy, hydroxy, and amino. $R^4$ is selected from the group consisting of H, optionally-substituted $C_1$–$C_4$ alkyl, $C_1$–$C_4$ alkenyl, and $C_1$–$C_4$ alkoxy. $R^5$ is selected from the group consisting of H and $C_1$–$C_4$ alkyl.

For compounds having Structure 7 or 7A, $R^1$ and $R^2$ may be the same or different and $R^1$ and $R^2$ are selected from the group consisting of H, $C_1$–$C_4$ alkyl, $C_1$–$C_4$ alkenyl, $C_1$–$C_4$ alkoxy, amino, hydroxy, trifluoromethyl and halogen. X is selected from the group consisting of O, N and $CH_2$, and $R^3$ is selected from the group consisting of optionally-substituted $C_1$–$C_4$ alkylamino and $C_1$–$C_4$ alkylimino.

For compounds having Structure8 or 8A, $R^1$ and $R^2$ may be the same or different and $R^1$ and $R^2$ are selected from the group consisting of H, $C_1$–$C_4$ alkyl, $C_1$–$C_4$ alkenyl, $C_1$–$C_4$ alkoxy, amino, hydroxy, trifluoromethyl and halogen. $R^3$ and $R^4$ may be the same or different and $R^3$ and $R^4$ are selected from the group consisting of H and $C_1$–$C_4$ alkyl.

For compounds having Structure 9 or 9A, $R^1$ and $R^2$ may be the same or different and $R^1$ and R2 are selected from the group consisting of H, $C_1$–$C_4$ alkyl, $C_1$–$C_4$ alkenyl, $C_1$–$C_4$ alkoxy, amino, hydroxy, trifluoromethyl and halogen. $R^3$ and $R^4$ may be the same or different and $R^3$ and $R^4$ are selected from the group consisting of H and $C_1$–$C_4$ alkyl.

For compounds having Structure 10 or 10A, $R^1$ and $R^2$ may be the same or different and $R^1$ and$^2$ are selected from the group consisting of H, $C_1$–$C_4$ alkyl, $C_1$–$C_4$ alkenyl, $C_1$–$C_4$ alkoxy, amino, hydroxy, trifluoromethyl and halogen. $R^3$ is selected from the group consisting of H and $C_1$–$C_4$ alkyl.

For compounds having Structure 11 or 11A, $R^1$, $R^2$, and $R^3$ may be the same or different and $R^1$, $R^2$, and $R^3$ are selected from the group consisting of H and optionally-substituted $C_1$–$C_{12}$ alkyl, $C_1$–$C_{12}$ alkenyl, and $C_1$–$C_{12}$ alkoxy In specific embodiments, $R^1$, $R^2$, and $R^3$ together form a ring of up to 16 atoms.

For compounds having Structure 12 or 12A, $R^1$ and $R^2$ may be the same or different and $R^1$ and $R^2$ are selected from the group consisting of H, $C_1$–$C_4$ alkyl, $C_1$–$C_4$ alkenyl, $C_1$–$C_4$ alkoxy, amino, nitro, hydroxy, trifluoromethyl and halogen.

For compounds having Structure 13 or 13A, $R^1$ is selected from the group consisting of H, optionally-substituted $C_1$–$C_4$ alkyl, $C_1$–$C_4$ alkenyl, $C_1$–$C_4$ alkoxy, hydroxy, and amino. $R^2$ is selected from the group consisting of H and optionally-substituted $C_1$–$C_4$ alkyl, $C_1$–$C_4$ alkenyl, and $C_1$–$C_4$ alkenoyl. $R^3$ is selected from the group consisting of H, $C_1$–$C_4$ alkyl, $C_1$–$C_4$ alkenyl, $C_1$–$C_4$ alkoxy, amino, hydroxy, trifluoromethyl and halogen.

For compounds having Structure 14 or 14A, $R^1$, $R^2$, and $R^3$ may be the same or different and $R^1$, $R^2$, and $R^3$ are selected from the group consisting of H, $C_1$–$C_4$ alkyl, $C_1$–$C_4$ alkenyl, $C_1$–$C_4$ alkoxy, amino, hydroxy, trifluoromethyl and halogen.

As used in the descriptions herein, the term "alkyl" refers to an aliphatic hydrocarbon, preferably a saturated hydrocarbon, either unbranched or branched. Preferably the alkyl group contains one to 12 carbons, more preferably from one to four carbons, such as, e.g., methyl, ethyl, n-propyl, iso-propyl, n-butyl, sec-butyl, iso-butyl and tertbutyl. The alkyl group may be optionally substituted with one or more functional groups which are attached commonly to such chains, preferably hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, and the like.

The term "alkenyl" denotes an alkyl group as defined above having at least one double bond, such as, e.g., vinyl, allyl, 1-propenyl, isopropenyl, 1-butenyl, 2-butenyl, 3-butenyl, methallyl, or 1,1-dimethylallyl.

The term "alkoxyl" denotes the group —OR, where R is alkyl or alkenyl as defined above, such as methoxy, ethoxy, n-propoxy, iso-propoxy, n-butoxy, sec-butoxy, iso-butoxy, or tert-butoxy and the like.

The term "hydroxy" refers to the group —OH.

The term "amino" refers to a group —N(R)R', in which R and R' are preferably H, but may optionally be independently substituted, for example with alkyl, aryl, or acyl groups.

The term "halogen" refers to a group which is selected from fluoro, chloro, bromo, and iodo, preferably fluoro or chloro.

The term "aryl" refers to a chain of atoms which form at least one aromatic ring, with the group indicated as "—Ar". The aromatic ring is preferably formed of carbon atoms, but may include one or more hetero atoms. The aryl group, preferably on the aromatic ring, may optionally be substituted with groups commonly attached to such chains, for example, hydroxy, halo, alkyl, alkenyl, thio, nitro, amino and the like.

The term "aryloxy" denotes a group —OAr, where Ar is aryl as defined above.

The term "araalkoxy" refers to a group —ORAr, in which R is an alkyl or alkenyl group and Ar is aryl as defined above.

The term "araalkyl" refers to a group —RAr, in which R is alkyl and Ar is aryl.

The term "alkylamino" refers to a group —N($R^1$)$R^2$, in which at least one of the R groups is an alkyl group, and one or both R groups may be optionally substituted.

Similarly, the term "alkylimine" indicates a group N=R, in which the R group is a branched or unbranched alkyl group which is optionally substituted, preferably with halo or sulfhydryl.

The term "nitro" refers to a group —$NO_2$.

The term "alkenoyl" denotes a group —C(O)R, in which R is an optionally substituted, branched or unbranched alkenyl group.

K. Administration

Although it is possible to administer the inhibitor alone, it is preferable to present an inhibitor as part of a pharmaceutical composition containing the active inhibitor compound and a carrier or excipient. In addition, as noted above, in some cases, the effect of administering an inhibitor of a global regulator of pathogenesis genes will be to make infecting bacteria more accessible to another antibacterial agent, or otherwise to increase the effectiveness of the administration of such other antibacterial agent. Therefore, in some cases it will be advantageous to administer an inhibitor of a global regulator of pathogenes or of other regulatory pathways in combination (either simultaneously or serially) with another traditional antibacterial agent, preferably one which has bacteriocidal effects.

The formulations of the present invention preferably contain at least one inhibitor of a global regulator of pathogenesis genes or other regulatory pathways and one or more pharmaceutically or therapeutically acceptable carriers or excipients. The inhibitor compound is in such amount that the combination constitutes a pharmaceutically or therapeutically effective dose or amount. The compounds can be prepared as pharmaceutically acceptable salts (i.e., non-toxic salts which do not prevent the compound from exerting its effect).

Carriers or excipient can be used to facilitate administration of the compound, for example, to increase the solubility of the compound. Solid carriers include, e.g., starch, lactose, dicalcium phosphate, microcrystalline cellulose, sucrose, and kaolin, and optionally other therapeutic ingredients. Liquid carriers include, e.g., sterile water, saline, buffers, polyethylene glycols, non-ionic surfactants, and edible oils such as corn, peanut and sesame oils, and other compounds described e.g., in the MERCK INDEX, Merck & Co., Rahway, N.J. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: *The Pharmacological Basis of Therapeutics*, 8th Ed., Pergamon Press. Methods for administration are discussed therein, e.g., for oral, intravenous, intraperitoneal, or intramuscular administration, subcutaneous, topically, and others.

These pharmaceutical compositions can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. For some compounds a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

The embodiments herein described are not meant to be limiting to the invention. Those of skill in the art will appreciate the invention may be practiced by using numerous compounds and by numerous methods all within the breadth of the claims. In particular, while the above description of the invention concentrates on bacterial pathogenesis, the invention also applies to global regulators of pathogenesis genes in other pathogenic microbes.

Other embodiments are within the following claims.

What we claim is:

1. A method of screening for an inhibitor of a global regulator of pathogenesis genes, comprising determining if any of a plurality of different test compounds alters the level of activity of said global regulator.

2. The method of claim 1, comprising determining if said test compound alters the level of expression of said global regulator.

3. The method of claim 2, comprising the steps of:
   a) detecting the transcriptional or translational product of a hybrid DNA construct comprising a regulatory region of a gene encoding a global regulator of pathogenesis genes transcriptionally linked with a reporter gene, and
   b) determining whether the amount of the transcriptional or translational product of said reporter gene differs in the presence and absence of any of said plurality of different test compounds,
   wherein said hybrid DNA construct is incorporated into a bacterium.

4. The method of claim 3, wherein said regulatory region of a gene encoding a global regulator of pathogenesis genes comprises a P3 promoter.

5. The method of claim 2, wherein said global regulator of pathogenesis genes is from a Staphylococcus strain.

6. The method of claim 5, wherein said Staphylococcal global regulator is from *Staphylococcus aureus*.

7. The method of claim 5, wherein said global regulator is encoded by the agr locus.

8. The method of claim 5, wherein said global regulator is encoded by the xpr gene.

9. The method of claim 5, wherein said global regulator is encoded by the sar gene.

10. The method of claim 5, wherein said global regulator is encoded by the sae gene.

11. A method of screening for an inhibitor of a Staphylococcal global regulator of pathogenesis genes, comprising contacting a plurality of different test compounds with said Staphylococcal strain, and determining if any of said plurality of different test compounds alters the level of expression of an RNAIII transcript.

12. The method of claim 11 wherein said Staphyloccocal strain is *Staphylococcus aureus*.

13. The method of claim 11, further comprising the steps of:
   a) detecting the transcriptional or translational product of a hybrid DNA construct comprising a regulatory region of a gene encoding RNAIII transcriptionally linked with a reporter gene, and
   b) determining whether the amount of the transcriptional or translational product of said reporter gene differs in the presence and absence of any of said plurality of different test compounds,
   wherein said hybrid DNA construct is incorporated into a bacterium.

14. The method of claim 13, wherein said regulatory region comprises a P3 promoter.

15. The method of either of claims 11 or 12, wherein the level of RNAIII expression is reduced.

* * * * *